US012606936B2

(12) United States Patent
Chen et al.

(10) Patent No.: US 12,606,936 B2
(45) Date of Patent: Apr. 21, 2026

(54) COMPOSITIONS AND METHODS FOR MAKING NOVEL T-CELL RECEPTORS

(71) Applicant: VCreate, Inc., San Carlos, CA (US)

(72) Inventors: Binbin Chen, Menlo Park, CA (US);
Ethan Fast, Menlo Park, CA (US)

(73) Assignee: VCreate, Inc., San Carlos, CA (US)

( * ) Notice: Subject to any disclaimer, the term of this patent is extended or adjusted under 35 U.S.C. 154(b) by 953 days.

(21) Appl. No.: 17/863,200

(22) Filed: Jul. 12, 2022

(65) Prior Publication Data

US 2023/0071148 A1 Mar. 9, 2023

Related U.S. Application Data

(60) Provisional application No. 63/344,221, filed on May 20, 2022, provisional application No. 63/300,905, filed on Jan. 19, 2022, provisional application No. 63/222,130, filed on Jul. 15, 2021.

(51) Int. Cl.
| | |
|---|---|
| *C40B 30/06* | (2006.01) |
| *A61K 40/11* | (2025.01) |
| *A61K 40/32* | (2025.01) |
| *C07K 14/725* | (2006.01) |

(52) U.S. Cl.
CPC .............. *C40B 30/06* (2013.01); *A61K 40/11* (2025.01); *A61K 40/32* (2025.01); *C07K 14/7051* (2013.01)

(58) Field of Classification Search
None
See application file for complete search history.

(56) References Cited

U.S. PATENT DOCUMENTS

| | | |
|---|---|---|
| 2019/0062450 A1 | 2/2019 | De Palma et al. |
| 2020/0371088 A1 | 11/2020 | Birnbaum et al. |
| 2021/0189336 A1 | 6/2021 | Primo Ramos et al. |

FOREIGN PATENT DOCUMENTS

| | | |
|---|---|---|
| WO | WO 2011/034969 | 3/2011 |

OTHER PUBLICATIONS

Rydzek et al. (Feb. 1, 2019) Molecular Therapy vol. 27 pp. 287 to 299 (Year: 2019).*
Dobson et al, Antigen identification and high-throughput interaction mapping by reprogramming viral entry, 2021, bioRxiv doi.org/10.1101/2021.09.18.460796.
Hansen et al, Translational and basic applications of peptide-MHCI single chain trimers, 2010, Trens Immunol vol. 31, pp. 363-369.
Ignatowicz et al, Cell surface expression of class II MHC proteins bound by a single peptide, 1995, J. Immunol. vol. 154, pp. 3852-3862.
Kotsiou et al, Properties and applications of single-chain major histocompatibility complex class I molecules, 2011, Antioxid Redox Signal vol. 15, pp. 645-655.
Mottez et al, Cells expressing a major histocompatibility complex class I molecule with a single covalently bound peptide are . . . , 1995, J. Exp. Med. vol. 181, pp. 493-502.
Uger et al, Creating CTL targets with epitope-linked B2-microglobulin constructs, 1998, J. Immunol. vol. 160, pp. 1598-1605.
Yu et al, Cutting Edge: single-chain trimers of MHC class I molecules from stable structures that potently stimulate antigen . . . , 2002, J. Immunol. vol. 168, pp. 3145-3149.
Yu et al, Systemic discovery of receptor-ligand biology by engineered cell entry and single-cell genomics, 2021, bioRxiv doi.org/10.1101/2021.12.13.472464.
Zhang et al, Transgenic TCR expression: comparison of single chain with full-length receptor constructs for T-cell function, 2004, Cancer Gen Therap vol. 11, pp. 487-496.
Zhao et al, Use of single chain MHC technology to investigate co-agonism in human CD8+ T cell activation, 2019, J Vis Exp vol. 144, e59126.
Bosch et al, Precise genome engineering in *Drosophila* using prime editing, 2021, Proc Natl Acad Sci vol. 118, e2021966118.
Jones et al., Empirical and rational design of T cell receptor-based immunotherapies, 2021, Front. Immunol. vol. 11, Article 585385.
Miyake et al, Trogocytosis of peptide-MHC class II complexes from dendritic cells confers antigen-presenting ability on basophils, 2017, Proc Natl Acad Sci vol. 114, pp. 1111-1116.

* cited by examiner

*Primary Examiner* — Christian C Boesen
(74) *Attorney, Agent, or Firm* — HelixIP LLP

(57) ABSTRACT

The disclosure relates generally to the field of T-cell receptors or T-cell receptor mimics, and methods for obtaining novel T-cell receptors or novel T-cell receptor mimics. The compositions and methods described identify pairs of T-cell receptors and antigens. The compositions and methods allow high throughput analysis so that many antigens can be paired with a large repertoire of T-cell receptors.

20 Claims, No Drawings

Specification includes a Sequence Listing.

1

COMPOSITIONS AND METHODS FOR MAKING NOVEL T-CELL RECEPTORS

REFERENCE TO SEQUENCE LISTING, TABLE OR COMPUTER PROGRAM

The official copy of the Sequence Listing is submitted as an ASCII formatted text file via EFS-Web, with a file name of "VC0005_ST26.xml", a creation date of Nov. 7, 2022, and a size of 23 kilobytes. The Sequence Listing filed via EFS-Web is part of the specification and is incorporated in its entirety by reference herein.

BACKGROUND OF THE DISCLOSURE

Immune cells are a group of heterogeneous cells involved in many important immune functions including defending pathogens, regulating inflammation, and clearing cancer cells. Main classes of immune cells include T-cells, B-cells, macrophages, neutrophils, natural killer (NK) cells, and dendritic cells. Though they differ in functions and morphologies, immune cells are all regulated positively or negatively by their surface receptors.

The T cell receptor (TCR) is a molecule found on the surface of T lymphocytes (i.e. T cells) that is responsible for recognizing antigens bound to major histocompatibility complex (MHC) molecules. The TCR is a heterodimer composed of two different protein chains. In most T cells (about 95%), these two protein chains are termed the alpha and beta chains. However, in a small percentage of T cells (about 5%), these two protein chains are termed the gamma and delta (gamma/delta) chains.

Humans have billions of T cell receptors that provide a major component of adaptive immune systems, and T cell receptor responses have been demonstrated to provide important contributions to protection from diseases including viral infections, cancer, and autoimmunity.

There is considerable interest in being able to discover T-cell receptors for specific antigens. Such T-cell receptors are useful as research tools and for diagnostic and therapeutic applications. However, the identification of such useful T-cell receptors is difficult and once identified, these T-cell receptors often require considerable redesign before they are suitable for therapeutic applications in humans.

SUMMARY

In an aspect, the disclosure relates to compositions and methods for identifying receptors or receptor mimics (e.g., chimeric receptors) that bind to certain ligands. The compositions and methods described herein can allow for high-throughput analysis. High diversity repertoires of receptors (e.g. immune cell receptors) may be screened against a library of ligands to identify pairs of receptor and ligand that interact with one another. Each nucleic acid encoding each receptor in the repertoire can be associated with a bar code that identifies the receptor encoded by the nucleic acid. Each nucleic acid encoding each ligand can also be associated with a barcode that will identify the ligand encoded by the nucleic acid.

In an aspect, the disclosure relates to compositions and methods for identifying immune cell receptors or immune cell receptor mimics (e.g., chimeric antigen receptors) that bind to certain ligands. The compositions and methods described herein can allow for high-throughput analysis. High diversity repertoires of immune cell receptors (e.g. T-cell receptors) may be screened against a library of ligands (e.g. antigens) to identify pairs of receptor and ligand that interact with one another. Each nucleic acid encoding each receptor in the repertoire can be associated with a bar code that identifies the receptor encoded by the nucleic acid. Each nucleic acid encoding each ligand can also be associated with a barcode that will identify the ligand encoded by the nucleic acid.

A wide range of immune cells and/or immune cell receptors can used with the methods described in this disclosure. For T-cells, applicable receptors include alpha beta T-cell receptor, gamma delta T-cell receptor, CD43, CD44, CD45, LFA1, CD4, CD8, CD3, LAT, CD27, CD96, CD28, TIGIT, ICOS, BTLA, HVEM, 4-1BB, OX40, DR3, GITR, CD30, SLAM, CD2, 2B4, TIM1, TIM2, TIM3, CD226, CD160, LAG3, LAIR1, CD112R, CTLA-4, PD-1, PD-L1, PD-L2. For NK-cells, applicable receptors include TRAIL, CD16, NKp30ab, NKGC, NKG2D, 2B4, DNAM-1, NKG2A, KIRs, CD137, OX40, CD27. For B-cells, applicable receptors include Siglec-10, LILRB/PIR-B, CD31, FcγRIIIB, CD19, CD20, CD22, CD25, CD32, CD40, CD47, CD52, CD80, CD86, CD267, CD268, CD268, B-cell receptor, antibody, IgM, IgD, IgG, IgA, IgE. For Dendritic cells, applicable receptors include DNGR-1, MICL, CLEC1, CLEC12B, LOX1, Mannose receptors, DC-SIGN, L-SIGN, SIGN-R1, LSECtin, CIRE, Langerin, MGL, Scavenger receptor (SR), DC-ASGPR, DC-STAMP, CD80/86, TLR, FIRE, FcR, DEC205, BDCA-2, Dectin-2, DCIR, and chemokine receptors. For macrophages, applicable receptors include CD300a, TREM2/DAP12, Bal-1, TIM4, CR3, SCARF1, CD36, MARCO, Scavenger Receptor A1, RAGE, Axl, Mer, Tyro3, CD93, Stabilin2, DNGR-1, SIRP. For neutrophils, applicable receptors include CXCR1, FcγRIIIB, FcγRII, CR3, CR1, C3aR, TNFR, TLR2/6, C5aR. Other receptors (e.g., G protein coupled receptors, ion channel-linked (ionotropic) receptors, and/or enzyme linked receptors) can also be used in the methods and compositions of this disclosure. Any immune cell that can be used herein including, for example, T-cells, B-cells, Natural Killer cells, dendritic cells, macrophages, monocytes, and/or neutrophils.

In an aspect, a repertoire of receptors described above, can be engineered into a phagocytic cell such as, for example, a macrophage, a dendritic cell, a neutrophil, and/or a THP-1 cell. Receptors of interest can be engineered with their endogenous intracellular activation domains or with phagocytosis-related intracellular activation domains (e.g. Fc receptor intracellular domain and CD19 intracellular domain). Extracellular domains of receptors can be wildtype or modified versions of the extracellular domain of the receptor of interest.

In an aspect, a repertoire of receptors can be engineered into an immune cell (e.g., T-cells, Natural Killer cells, B-cells, macrophages, neutrophils, dendritic cell, etc.). The repertoire of receptors is expressed on the surface of the immune cells (e.g., T-cells, Natural Killer cells, B-cells, macrophages, neutrophils, dendritic cell, etc.) and trogocytosis is used to segregate receptors with antigens/ligands for the receptor. Most immune cells are capable of trogocytosis including, for example, T-cells, macrophages, B-cells, neutrophils, natural killer (NK) cells, monocytes, and dendritic cells. Receptors of interest can be introduced with their endogenous intracellular activation domains or with trogocytosis-related intracellular activation domains (e.g. Fc receptor intracellular domain and TCR intracellular domain). Extracellular domains of receptors can be wildtype or modified versions of the receptor of interest.

Antigens/ligands for the receptor of interest can be a peptide, a MHC-peptide complex, a fragment, a chimera, or a whole protein. The antigen/ligand can also be a carbohydrate, fatty acid or lipid, or small molecule. Antigens/ligands can be associated with antigen presenting cell surface by covalent or noncovalent attachment. When the antigens/ligands are polypeptides, they can be anchored to the antigen presenting cell surface with their native transmembrane domains or with a synthetic transmembrane domain. A synthetic transmembrane domain can be fused to the antigen/ligand extracellular domain by engineering a DNA sequence to operably link the synthetic transmembrane domain DNA sequence with the DNA sequence encoding the desired part, portion or whole of the antigen/ligand. Exemplary synthetic transmembrane domains include wild-type or modified transmembrane domains from CD2, CD3d, CD3g, CD3z, CD4, CD8A, CD8B, CD22, CD27, CD28, CD40, CD79a, CD79b, CD80, CD84, CD86, CD137, CD244, CRACC, CRTAM, CLTA-4, MHC-I, MHC-II, platelet-derived growth factor receptor, FCGR1A, FCGR2A, FCG2B, FCGR3A, FCRL1, FCRL2, FCRL3, FCRL4, FCRL5, FCRL6, KIR2DL1, KIR2DL2, KIR2DL3, KIR2DL4, KIR2DL5A, KIR2DL5B, KIR3DL1, KIR3DL2, KIR3DL3, LAG3, GITR, OX40, PD-1, PD-L1, PD-L2, TLR, SLAMF, LILRB1, LILRB2, NKG2A, NKG2C, NKG2D, TIGIT, IgG, IgM, IgA, IgE, IgD, or immunoglobulin. A repertoire of antigen/ligands can be made and engineered into the antigen/ligand presenting cell. Optionally, variation in the antigen/ligand library can be made by introducing genetic mutations into desired locations (e.g., randomly, or site specific) on the antigen/ligand of interest. Genetic mutations can be substitution, deletion, insertion, and rearrangement of DNA fragments. Specific genetic mutations of choice can be generated randomly, enriched in the region of interest (e.g. interacting domains of the ligand), or recommended by a computational algorithm. Examples of computational algorithms to recommend genetic mutation strategies include protein structure analysis, computational docking, molecular dynamics simulation, regression, statistics-based classifier, random forest, support vector machine, and neural networks.

The antigen/ligand binding portion of immune cell receptors or immune cell receptor mimics can be fused to the intracellular domains of a Fc receptor. Immune cell receptor mimics refer to antibody or antibody fragments that can bind and interact with MHC::antigen complexes (academic.oup-.com/abt/article/2/1/22/5290150). Optionally, these chimeric receptors can include the transmembrane domain of the Fc receptor, or the chimeric receptor can have a different transmembrane domain. These chimeric receptors will have the binding specificity of the immune cell receptor and can activate macrophages to phagocytose a target that displays the antigen bound by the immune cell receptor. The macrophage/monocyte cell with the chimeric TCRs can also be engineered to express one or more of CD28, CD137, CD3, B7.1, CD19 intracellular activation domain, CD64 intracellular activation domain, CD32 intracellular activation domain, CD16 intracellular activation domain, CD23 intracellular activation domain, or Lck activation domain. These additional modifications can be included in the chimeric immune receptor Fc fusion, e.g., as co-stimulatory domains, or can be individually expressed in the monocyte/macrophage cell. When the engineered monocyte/macrophage phagocytoses a cell displaying the appropriate antigen this can produce a macrophage that has an immune cell receptor with its barcode, and an antigen/ligand with its barcode. Sequencing of such individual macrophages can identify the immune cell receptor-antigen/ligand pairs.

The antigen binding portion of T-cell receptors or T-cell receptor mimics can be fused to the intracellular domains of a Fc receptor. T-cell receptor mimics refer to antibody or antibody fragments that can bind and interact with MHC::antigen complexes (academic.oup.com/abt/article/2/1/22/5290150). Optionally, these chimeric receptors can include the transmembrane domain of the Fc receptor, or the chimeric receptor can have a different transmembrane domain. These chimeric receptors will have the binding specificity of the T-cell receptor and can activate macrophages to phagocytose a target that displays the antigen bound by the T-cell receptor. The macrophage/monocyte cell with the chimeric TCRs can also be engineered to express one or more of CD28, CD137, CD3, B7.1, CD19 intracellular activation domain, CD64 intracellular activation domain, CD32 intracellular activation domain, CD16 intracellular activation domain, CD23 intracellular activation domain, or Lck activation domain. These additional modifications can be included in the chimeric TCR-Fc fusion, e.g., as co-stimulatory domains, or can be individually expressed in the monocyte/macrophage cell. When the engineered monocyte/macrophage phagocytoses a cell displaying the appropriate antigen this can produce a macrophage that has a T-cell receptor with its barcode, and an antigen with its barcode. Sequencing of such individual macrophages can identify the T-cell receptor-antigen pairs.

The antigen/ligand library can be made in an antigen presenting cell (e.g., a K562 cell line), the antigen or ligand can be encoded by a nucleic acid encoding the antigen or ligand optionally with a bar code, or a recombinant MHC protein fused to an antigen/ligand polypeptide and a bar code. When the antigen is a non-polypeptide antigen, the antigen presenting cell can be engineered to make the antigen/ligand and display it on the surface of the antigen presenting cell. Alternatively, the antigen/ligand can be made outside of the antigen presenting cell and then associated with the surface of the antigen presenting cell. Polypeptide fragments from each antigen/ligand that can be presented can be identified by antigen-MHC binding experiments, mass spectrometry experiments, sliding windows of full protein sequences (8-25 per window), or fragments of known proteins predicted to be presentable with a computer algorithm. These presentable peptide fragments from the antigen can be fused with an appropriate MHC molecule to make a library of presented antigens. The antigen presenting cell can be the K562 cell line (a human immortalized myelogenous leukemia cell line) or engineered HEK293 cell lines. The MHC—antigen polypeptide fusions can be introduced into K562 cells to make a library of antigen peptides. Optionally the K562 cells can be engineered with an optical reporter, e.g., GFP.

The immune cell receptor repertoire in macrophage cells (e.g., THP-1 cells which is a human monocytic cell line derived from an acute monocytic leukemia) can be mixed with the antigen library in the K562 cells. The macrophage cells (e.g., THP-1 cells) with immune receptor chimeric receptors or immune cell receptor mimics that bind an antigen peptide:MHC fusion (or the antigen/ligand) can phagocytose the K562 cells displaying the appropriate peptide:MHC fusion (or antigen/ligand). The macrophage cells (e.g., THP-1 cells) with a phagocytosed K562 cell can be isolated and individually sequenced to identify the bar codes associated with the immune cell receptor and the antigen/ligand. When the K562 cells include a reporter, that reporter can be used to screen for macrophage cells (e.g., THP-1 cells) that have phagocytosed a K562 cell using, for example, flow cytometry. Alternatively, the antigen:MHC fusion and the immune receptor chimeric receptors can be directly sequenced to identify the immune cell receptor and antigen/ligand pair.

The T-cell receptor repertoire in macrophage cells (e.g., THP-1 cells which is a human monocytic cell line derived from an acute monocytic leukemia) can be mixed with the antigen library in the K562 cells. The macrophage cells (e.g., THP-1 cells) with TCR chimeric receptors or T-cell receptor mimics that bind an antigen peptide:MHC fusion can phagocytose the K5662 cells displaying the appropriate peptide:MHC fusion. The macrophage cells (e.g., THP-1 cells) with a phagocytosed K562 cell can be isolated and individually sequenced to identify the bar codes associated with the T-cell receptor and the antigen. When the K562 cells include a reporter, that reporter can be used to screen for macrophage cells (e.g., THP-1 cells) that have phagocytosed a K562 cell using, for example, flow cytometry. Alternatively, the antigen:MHC fusion and the TCR chimeric receptors can be directly sequenced to identify the TCR and antigen pair.

In an aspect, phagocytosis by the macrophages/monocytes/dendritic cells/neutrophils with the chimeric TCRs can be facilitated by stimulating differentiation of the macrophage/monocyte/dendritic cell/neutrophil (if it is not a terminally differentiated cell), e.g., for macrophages/monocytes, differentiation using T-cell macrophage hybridomas, blocking the CD47 pathway, or blocking the CD24 pathway.

Alternatively, many immune cells including T-cells, B-cells, natural killer cells, and macrophages rapidly exchanges a fraction of cell content and membrane with target cells in a cell contact-dependent and activation-dependent manner (https://www.mdpi.com/2073-4409/10/5/1255). This phenomenon is termed "Trogocytosis." Specifically, T-cells undergo trogocytosis when activated by antigen antigens presented by antigen presenting presentation cells (https://pubmed.ncbi.nlm.nih.gov/17406507/, https://pubmed.ncbi.nlm.nih.gov/10542149/). Trogocytosis cell membrane exchange between two cells is bi-directional. This disclosure describes a method to transfer antigen/ligand or receptor (e.g., T-cell receptor) information between a library of T-cells and a library of antigen-presenting cells using trogocytosis and membrane-bound RNA/DNA barcodes. By anchoring antigen/ligand barcodes or receptor (e.g., TCR) barcode DNA or RNA to either antigen presentation cell (APC) or cell membrane, activation triggered trogocytosis naturally transfers barcode DNA or RNA between cells for downstream sequencing analysis.

An antigen/ligand library can be made in an antigen presenting cell (e.g., a K562 cell line), including a nucleic acid encoding a recombinant MHC protein fused to an antigen polypeptide (or the antigen/ligand) and a bar code. Polypeptide fragments from each antigen that can be presented can be identified by antigen-MHC binding experiments, mass spectrometry experiments, sliding windows of full protein sequences (8-25 per window), or fragments of known proteins predicted to be presentable with a computer algorithm. These presentable peptide fragments from the antigen can be fused with an appropriate MHC molecule to make a library of presented antigens. The antigen presenting cell can be any antigen presenting cell including, for example, the K562 cell line (a human immortalized myelogenous leukemia cell line) or engineered HEK293 cell lines. The MHC—antigen polypeptide fusions can be introduced into K562 cells to make a library of antigen peptides. To anchor antigen DNA or RNA barcodes to cell membrane, K562 cells or similar APCs express membrane-bound DNA-binding or RNA-binding protein(s) and antigen barcode DNA or RNA with affinity for its corresponding membrane-bound DNA-binding or RNA-binding protein(s). DNA-binding or RNA-binding protein(s) can be fused to or independent of MHC protein. Antigen barcodes can be fused to or independent of MHC protein. Optionally the K562 cells can be engineered with an optical reporter, e.g., GFP or stained with cell-membrane dye, e.g. Dil.

The T-cell library can contain T-cells with a diverse set of immune cell receptors (e.g., T-cell receptors). Similar to antigen presentation cells described above, T-cells can express a membrane-bound DNA binding or RNA-binding protein(s) and immune receptor (e.g., TCR) barcode DNA or RNA with affinity for its corresponding membrane bound DNA-binding or RNA-binding protein(s). DNA-binding or RNA-binding protein(s) can be fused to or independent of immune receptor protein (e.g., TCR). Antigen barcodes can be fused to or independent of the immune receptor protein (e.g., TCR). Optionally T-cell cells can be engineered with an optical reporter, e.g., membrane-bound GFP or stained with cell-membrane dye, e.g. Dil. When the engineered T-cell interacts with a cell displaying the appropriate antigen it can capture the barcode presented on the APC surface by biting off a piece of the cell membrane through trogocytosis. Activated T-cells can be sorted or enriched through antigen presenting cell membrane markers including transfected/transduced fluorescent protein, membrane-bound dye or APC surface marker or through T-cell activation markers including CD11a, CD69, CD70 CD71, CD25, CD26, CD27, CD28, CD30, CD40L, CD86, CD134, CD154, PD1, IL-2, NKG2D, TNF-alpha, IFN-gamma or HLA-DR. Through trogocytosis, activated T-cells contain DNA or RNA barcodes of corresponding antigens. DNA or RNA sequencing of such T-cells can identify the immune cell receptor sequence (e.g., TCR), antigen sequence and T-cell receptor-antigen relationship.

The immune cell receptor repertoire (e.g., TCR repertoire) in the engineered cell library cells (e.g., Jurkat) can be mixed with the antigen library in the K562 cells. The receptor repertoire cells interact with the K562 cells displaying the appropriate antigen/ligand (e.g., peptide-MHC fusion), resulting in barcode transfer through trogocytosis. The cells that have been activated by an APC (e.g. K562 cells) can be isolated and individually sequenced to identify the bar codes associated with the receptor (e.g., immune cell receptor such as a TCR) and the antigen. When the K562 cells include a reporter, that reporter can be used to screen for receptor-cells (e.g., Jurkat cells) that have interacted with a K562 cell using flow cytometry or magnetic bead enrichment. The antigen barcode and the receptor (e.g., TCR)/receptor mimic (e.g., CAR) barcode can be directly sequenced to identify the receptor and antigen pairs as sorted T-cells contain both barcodes.

Similarly, receptor-antigen/ligand interaction pairs can also be extracted by sequencing receptor cells after trogocytosis. Antigen/ligand-cells can be engineered to have an optical reporter, e.g. membrane-bound GFP or stained with a dye, e.g. Dil. Receptor cells (e.g., K562 cells) can experience a trogocytosis event with a antigen/ligand cell and can retain a fragment of the antigen/ligand-cell membrane with the optical reporter or dye (https://pubmed.ncbi.nlm.nih-.gov/30700903/). Such K562 cells can be sorted out via flow cytometry or enriched by magnetic beads based on the membrane bound optical reporter or dye. The antigen barcode and the receptor (e.g., TCR)/receptor mimic (e.g., CAR) barcode can be directly sequenced to identify the receptor (e.g., TCR) and antigen/ligand pairs as sorted APC/K562 cells contain both barcodes.

In an aspect, the antigen/ligand can be engineered into a retrovirus (e.g., a lentivirus) having a mutated viral envelope glycoprotein comprising at least one mutation that diminishes its native function, a nucleic acid encoding an pegRNA (a prime editing guide RNA), and a nucleic acid encoding a non-viral membrane-bound protein comprising a structure: S-ETD-LGD-IRES-R, wherein S encodes a signal sequence, ETD encodes an extracellular targeting domain; LGD encodes the antigen/ligand, IRES encodes an internal ribosome entry site, and R encodes a reporter (e.g., a fluorescent protein or a selection marker such as antibiotic resistance). The IRES and R are optional, and the nucleic acid can encode S-ETD-LGD. The IRES sequence can be substituted by a 2A self-cleaving peptide sequence (T2A, P2A, F2A, and E2A) which similarly allows co-expression of two genes with one promoter. The receptor displaying cells that are paired with the retrovirus library of antigen/ligand are engineered to include an insertion site for the pegRNA adjacent to or near the nucleic acid encoding the receptor. The pegRNA (a prime editing guide RNA) inserts a barcode corresponding to the antigen/ligand near or adjacent to the nucleic acid encoding the receptor. Sequencing of cells transduced by the retrovirus will identify this barcode in the context of sequences that identify the receptor and ligand pairs.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as an antecedent basis for use of such exclusive terminology as "solely," "only" and the like in connection with the recitation of claim elements or use of a "negative" limitation. Numerical limitations given with respect to concentrations or levels of a substance are intended to be approximate, unless the context clearly dictates otherwise. Thus, where a concentration is indicated to be (for example) 10 micrograms ("μg"), it is intended that the concentration be understood to be at least approximately or about 10 μg.

Recombinant techniques that are included in this description include, for example, conventional techniques in molecular biology, protein biochemistry, cell biology, immunology, microbiology and recombinant DNA are used. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology, all of which are incorporated by reference in their entirety for all purposes.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

As used herein, the term "antigen" refers to substances that are capable, under appropriate conditions, of inducing a specific immune response and of reacting with the products of that response, such as, with specific antibodies or specifically sensitized T-lymphocytes, or both. Antigens may be soluble substances, such as toxins, foreign proteins, mutated proteins, self proteins, or particulates, such as bacteria and tissue cells; however, only the portion of the protein or polysaccharide molecule known as the antigenic determinant (epitopes) combines with the antibody or a specific receptor on a lymphocyte.

As used herein, the term "binding specificity" of a TCR refers to the identity of the antigen to which the TCR binds, preferably to the identity of the epitope to which the TCR binds and activates T-cells.

As used herein, "complementarity determining region" or "CDR" refers to a region of a TCR that is primarily responsible for binding to an epitope of an antigen or an antigen:WIC complex. CDRs are also referred to as hypervariable regions. The CDRs of each TCR are typically referred to as CDR1, CDR2, and CDR3, numbered sequentially starting from the N-terminus, and are also typically identified by the chain in which the particular CDR is located. TCRs with different specificities (i.e. different combining sites for different antigens) have different CDRs. Only a limited number of amino acid positions within the CDRs are directly involved in antigen binding. These positions within the CDRs are called specificity determining residues (SDRs).

As used herein, the term "epitope" refers to the site on an antigen or hapten to which specific B cells and/or T cells respond. The term is also used interchangeably with "antigenic determinant" or "antigenic determinant site". Epitopes include that portion of an antigen or other macromolecule capable of forming a binding interaction that interacts with the variable region binding pocket of an antibody.

As used herein, the term "heterologous" when used with reference to portions of a polynucleotide indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a "heterologous" polypeptide or protein refers to two or more subsequences that are not found in the same relationship to each other in nature.

As used herein, the term "host cell" refers to a prokaryotic or eukaryotic cell into which the vectors of the invention may be introduced, expressed and/or propagated. A microbial host cell is a cell of a prokaryotic or eukaryotic micro-organism, including bacteria, yeasts, microscopic fungi and microscopic phases in the life-cycle of fungi and slime molds. Typical prokaryotic host cells include various strains of E. coli. Typical eukaryotic host cells are yeast or filamentous fungi, or mammalian cells, such as Chinese hamster ovary cells, murine NIH 3T3 fibroblasts, human embryonic kidney 193 cells, or rodent myeloma or hybridoma cells.

As used herein, the term "humanized" forms of non-human proteins (e.g., murine TCRs) are chimeric proteins which contain minimal sequence derived from non-human homologs of the protein. For the most part, humanized proteins are human TCRs in which variable region residues of the recipient are replaced by variable region residues (e.g., CDRs) from a non-human species (donor TCR) such as mouse, rat, rabbit or nonhuman primate having the desired specificity, affinity, and capacity.

As used herein, the term "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term "isolated" refers to a nucleic acid or polypeptide separated not only from other nucleic acids or polypeptides that are present in the natural source of the nucleic acid or polypeptide, but also from polypeptides, and preferably refers to a nucleic acid or polypeptide found in the presence of (if anything) only a solvent, buffer, ion, or other component normally present in a solution of the same. The terms "isolated" and "purified" do not encompass nucleic acids or polypeptides present in their natural source.

As used herein, the term "mammal" refers to warm-blooded vertebrate animals all of which possess hair and suckle their young.

As used herein "MHC molecules," "MHC proteins" or "HLA proteins" are used interchangeably and are to be understood as meaning, in particular, proteins capable of binding peptides resulting from the proteolytic cleavage of protein antigens and representing potential T cell epitopes, transporting them to the cell surface and presenting them to specific cells there, in particular naive T cells, cytotoxic T-lymphocytes, regulatory T-cells, or T-helper cells. The major histocompatibility complex in the genome comprises the genetic region whose gene products are expressed on the cell surface and are important for binding and presenting endogenous and/or foreign antigens, and thus for regulating immunological processes. The major histocompatibility complex is classified into two gene groups coding for different proteins: molecules of MHC class I and MHC class II. The molecules of the two MHC classes are specialized for different antigen sources. The molecules of MHC class I typically present but are not restricted to endogenously synthesized antigens, for example viral proteins and tumor antigens. The molecules of MHC class II present protein antigens originating from exogenous sources, for example bacterial products.

As used herein, the term "naturally occurring" means that the components are encoded by a single gene that was not altered by recombinant means and that pre-exists in an organism, e.g., in an antibody library that was created from naive cells or cells that were exposed to an antigen.

As used herein, the terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the term "purified" means that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

As used herein, the term "recombinant nucleic acid" refers to a nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of this disclosure.

As used herein, the term "recombinant polypeptide" refers to a polypeptide expressed from a recombinant nucleic acid, or a polypeptide that is chemically synthesized in vitro.

As used herein, the terms "repertoire" or ""library" refers to a library of genes encoding antibodies, T-cell receptors, or antibody fragments such as Fab, scFv, Fd, LC, $V_H$, or $V_L$, or a sub-fragment of a variable region, e.g., an exchange cassette, that is obtained from a natural ensemble, or "repertoire", of antibody genes present, e.g., in human donors, and obtained primarily from the cells of peripheral blood and spleen. In some embodiments, the human donors are "non-immune", i.e., not presenting with symptoms of infection. In the current invention, a library or repertoire often comprises members that are exchange cassette of a given portion of a V region.

As used herein, a "single chain TCR" is a single polypeptide chain that has both alpha and beta chains of a TCR or both gamma and delta chains of a TCR arranged so that the two TCR chains can form a TCR. The term further includes, but is not limited to, covalently linking TCR alpha and TCR beta or TCR gamma and TCR delta variable chain fragments with or without a linker. The single chain TCRs can optionally include CD3 or CD3 zeta signaling domains alone or in combination with a CD28 signaling domain.

As used herein, a "T-cell" is defined to be a hematopoietic cell that normally develops in the thymus. T-cells include, but are not limited to, natural killer T cells, regulatory T cells, helper T cells, cytotoxic T cells, memory T cells, gamma delta T cells and mucosal invariant T cells. T-cells also include but are not limited to CD8+ T-cells, CD4+ T-cells, Th1 T-cells, and Th2 T-cells. T-cells can be primary T-cells or T-cell lines.

As used herein, the term "T cell receptor' or "TCR" are used interchangeably and refer to a heterodimeric cell surface protein of the immunoglobulin super-family which is associated with invariant proteins of the CD3 complex involved in mediating signal transduction. The TCR is composed of two cognate protein chains: an alpha chain and a beta chain, or a gamma chain and a delta chain.

As used herein, the term "TCR library" refers to a polyclonal collection of vectors encoding TCRs or cells containing those vectors. A "TCR library" can include a collection of a subset or selection of vectors encoding TCRs. A "TCR library" can refer to a collection of the repertoire of TCRs that can be found in a subject. A "TCR library" can also refer to a subset of the repertoire of TCRs found in a subject.

The singular terms "a", "an", and "the" include plural referents unless context clearly indicates otherwise. Similarly, the word "or" is intended to include "and" unless the context clearly indicates otherwise. Numerical limitations given with respect to concentrations or levels of a substance, such as an antigen, are intended to be approximate. Thus, where a concentration is indicated to be at least (for example) 200 µg, it is intended that the concentration be understood to be at least approximately "about" or "about" 200 µg.

Novel Receptors

A wide range of immune cells and/or immune cell receptors can used with the methods described in this disclosure. For T-cells, applicable receptors include chimeric antigen receptor, alpha beta T-cell receptor, gamma delta T-cell receptor, CD43, CD44, CD45, LFA1, CD4, CD8, CD3, LAT, CD27, CD96, CD28, TIGIT, ICOS, BTLA, HVEM, 4-1BB, OX40, DR3, GITR, CD30, SLAM, CD2, 2B4, TIM1, TIM2, TIM3, CD226, CD160, LAG3, LAIR1, CD112R, CTLA-4, PD-1, PD-L1, PD-L2. For NK-cells, applicable receptors include TRAIL, CD16, NKp30ab, NKGC, NKG2D, 2B4, DNAM-1, NKG2A, KIRs, CD137, OX40, CD27. For B-cells, applicable receptors include Siglec-10, LILRB/PIR-B, CD31, FcγRIIIB, CD19, CD20, CD22, CD25, CD32, CD40, CD47, CD52, CD80, CD86, CD267, CD268, CD268, B-cell receptor, antibody, IgM, IgD, IgG, IgA, IgE. For Dendritic cells, applicable receptors include DNGR-1, MICL, CLEC1, CLEC12B, LOX1, Mannose receptors, DC-SIGN, L-SIGN, SIGN-R1, LSECtin, CIRE, Langerin, MGL, Scavenger receptor (SR), DC-ASGPR, DC-STAMP, CD80/86, TLR, FIRE, FcR, DEC205, BDCA-2, Dectin-2, DCIR, and chemokine receptors. For macrophages, applicable receptors include CD300a, TREM2/DAP12, Bal-1, TIM4, CR3, SCARF1, CD36, MARCO, Scavenger Receptor A1, RAGE, Axl, Mer, Tyro3, CD93, Stabilin2, DNGR-1, SIRP. For neutrophils, applicable receptors include CXCR1, FcγRIIIB, FcγRII, CR3, CR1, C3aR, TNFR, TLR2/6, C5aR. Other receptors (e.g., G protein coupled receptors, ion channel-linked (ionotropic) receptors, and/or enzyme linked receptors) can also be used in the methods and compositions of this disclosure. Ligands to be screened in this disclosure can be known ligands of the target receptor (e.g. PD-1L to PD-1 receptor), or whole protein with unknown affinity, or peptides with unknown affinity.

The compositions and methods described herein can be used to find novel pairs of antigens and T-cell receptors or T-cell receptor mimics. T-cell receptor mimics refers to antibody or antibody fragments that can bind to MHC-presented antigens. T-cell receptor repertoires are made in monocytes (e.g., a macrophage) or other phagocytosing cell type. The antigen binding portion of the T-cell receptor is fused to all or a portion of an Fc receptor, so that when this chimeric receptor binds antigen the macrophage will phagocytose the antigen. The nucleic acids encoding the TCR receptors or T-cell receptor mimics include barcodes that identify the TCR and co-activation domain (e.g. Fc domain). The TCR chimeric receptors or T-cell receptor mimics library can be expressed in an appropriate monocyte cell (e.g., a macrophage) or other phagocytosing cell types (e.g., neutrophils, dendritic cells, mast cells, etc.).

The compositions and methods described herein can be used to find novel pairs of other receptors and ligands (e.g., antigens). In addition to T-cell receptors and T-cell receptor mimics, other receptors may be used. For example, ion channel-linked (ionotropic) receptors, G protein-coupled (metabotropic) receptors, and enzyme-linked receptors can be coupled to the expression of the transgene. One class of receptor that can be used are immune receptors such as, for example, T-cell receptors, B-cell receptors (aka antigen receptor or immunoglobulin receptor), and innate immunity receptors.

T-cell receptors are heterodimers of two different polypeptide chains. In humans, most T cells have a T-cell receptor made of an alpha (α) chain and a beta (β) chain have a T-cell receptor made of gamma and delta (γ/δ) chains (encoded by TRG and TRD, respectively). Techniques and primers for amplifying nucleic acids encoding the T-cell receptor chains from lymphocytes are well known in the art and are described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. The TCR repertoires can be used as separate chains to form an antigen binding domain. The TCR repertoires can be converted to single chain antigen binding domains. Single chain TCRs can be made from nucleic acids encoding human alpha and beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/Aggen_David.pdf?sequence=1, all of which are incorporated by reference in their entirety for all purposes.

B-cell receptors include an immunoglobulin that is membrane bound, a signal transduction moiety, CD79, and an ITAM. Techniques and primers for amplifying nucleic acids encoding human antibody light and heavy chains are well-known in the art, and described in, for example, ProGen's Human IgG and IgM Library Primer Set, Catalog No. F2000; Andris-Widhopf et al., "Generation of Human Fab Antibody Libraries: PCR Amplification and Assembly of Light and Heavy Chain Coding Sequences," Cold Spring Harb. Protoc. 2011; Lim et al., Nat. Biotechnol. 31:108-117 (2010); Sun et al., World J. Microbiol. Biotechnol. 28:381-386 (2012); Coronella et al., Nucl. Acids. Res. 28:e85 (2000), all of which are incorporated by reference in their entirety for all purposes. Techniques and primers for amplifying nucleic acids encoding mouse antibody light and heavy chains are well-known in the art, and described in, for example, U.S. Pat. No. 8,143,007; Wang et al., BMC Bioinform. 7(Suppl):S9 (2006), both of which are incorporated by reference in their entirety for all purposes. The antibody repertoires can be used as separate chains in antigen binding domains, or converted to single chain antigen binding domains. Single chain antibodies can be made from nucleic acids encoding human light and heavy chains using techniques well-known in the art including, for example, those described in Pansri et al., BMC Biotechnol. 9:6 (2009); Peraldi-Roux, Methods Molc. Biol. 907:73-83 (2012), both of which are incorporated by reference in their entirety for all purposes. Single chain antibodies can be made from nucleic acids encoding mouse light and heavy chains using techniques well-known in the art including, for example, those described in Imai et al., Biol. Pharm. Bull. 29:1325-1330 (2006); Cheng et al., PLoS ONE 6:e27406 (2011), both of which are incorporated by reference in their entirety for all purposes.

Innate immunity receptors include, for example, the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105).

G-protein linked receptors also known as seven-trans-membrane domain receptors are a large family of receptors that couple receptor binding of ligand to cellular responses through G proteins. These G-proteins are trimers of $\alpha$, $\beta$, and $\gamma$ subunits (known as G$\alpha$, G$\beta$, and G$\gamma$, respectively) which are active when bound to GTP and inactive when bound to GDP. When the receptor binds ligand it undergoes a conformational change and allosterically activates the G-protein to exchange GTP for bound GDP. After GTP binding the G-protein dissociates from the receptor to yield a G$\alpha$-GTP monomer and a G$\beta\gamma$ dimer. G-protein linked receptors have been grouped together into classes which include, for example, Rhodopsin-like receptors, secretin receptors, metabotropic glutamate/pheromone receptors, fungal mating pheromone receptors, cyclic AMP receptors, and frizzled/smoothened receptors. G-protein receptors are used in a wide variety of physiological processes including detection of electromagnetic radiation, gustatory sense (taste), sense of smell, neurotransmission, immune system regulation, growth, cell density sensing, etc.

Enzyme linked receptors also known as a catalytic receptor, is a transmembrane receptor, where the binding of an extracellular ligand causes enzymatic activity on the intracellular side. Enzyme linked receptors have two domains joined together by a transmembrane portion (or domain) of the polypeptide. The two terminal domains are an extracellular ligand binding domain and an intracellular domain that has a catalytic function. There are multiple families of enzyme linked receptors including, for example, the Erb receptor family, the glial cell-derived neurotrophic factor receptor family, the natriuretic peptide receptor family, the trk neurotrophin receptor family, and the toll-like receptor family.

Ion channel linked receptors also known as ligand-gated ion channels are receptors that allow ions such as, for example, Na$^+$, K$^+$, Ca$^{2+}$ and Cl$^-$ to pass through the membrane in response to the binding of a ligand to the receptor. There are multiple families of ligand-gated ion channels including, for example, cationic cys-loop receptors, anionic cys-loop receptors, ionotropic glutamate receptors (AMPA receptors, NMDA receptors), GABA receptors, 5-HT receptors, ATP-gated channels, and PIP$_2$-gated channels.

T-cell receptor repertoires can be made from donors/patients who have appropriate HLA alleles (e.g., HLA-A02:01), from engineered cell lines (e.g., Jurkat cells), or synthesized from known sequences (e.g., GenBank). Diversity can be introduced to engineered cells via plasmids that introduce specific alpha and beta chain TCRs across a range of V and J genes. Combinations of CDR3, alpha, and beta genes can be put together in any of the following ways: (1) sampling known unpaired (e.g., beta or alpha) TCRs, optionally known to interact with an antigen target (2) sampling paired TCRs, optionally known to interact with an antigen target (3) starting from a known paired or unpaired TCR known to interact with an antigen target and mutating its CDR3 region in areas either known to be important to binding or known to be unimportant to binding.

Repertoires of other receptors also can be made from donors/patients who have appropriate HLA alleles (e.g., HLA-A02:01), or taken from appropriate cell lines, or synthesized from known sequences (e.g., sequences found in GenBank). Diversity can be introduced to the repertoire of receptors using methods known in the art (e.g., engineering mutations into the receptor, chain swapping, making chimeras of receptor chains, chain swapping for receptors made of two or more polypeptides, etc.).

DNA encoding receptors of interest can be synthesized individually or in a pooled library format. Variations (e.g., diversity) can be introduced to the receptor library or repertoire using genetic mutations introduced on any location of the receptor of interest. Alternatively, variation can be introduce by chain swapping techniques, or mixing segments of nucleic acids encoding the receptor (chain(s)) for example as done in some guided evolution methods. Genetic mutations can be substitution, deletion, insertion, and rearrangement of DNA fragments. Specific genetic mutations of choice can be generated randomly, enriched in the region of interest (e.g. interacting domains of the receptor), or recommended by a computational algorithm. Example computational algorithms to recommend genetic mutation strategies include protein structure analysis, computational docking, molecular dynamics simulation, regression, statistics-based classifier, random forest, support vector machine, and neural networks.

Antigens/ligands for the receptor of interest can be a peptide, an WIC-peptide complex, a fragment, a chimera, or a whole protein. The antigen/ligand can also be a carbohydrate, fatty acid or lipid, or small molecule. Antigens/ligands can be associated with antigen presenting cell surface by covalent or noncovalent attachment. When the antigens/ligands are polypeptides, they can be anchored to the antigen presenting cell surface with their native transmembrane domains or with a synthetic transmembrane domain. A synthetic transmembrane domain can be fused to the antigen/ligand extracellular domain by engineering a DNA sequence to operably link the synthetic transmembrane domain DNA sequence with the DNA sequence encoding the desired part, portion or whole of the antigen/ligand. Exemplary synthetic transmembrane domains include wild-type or modified transmembrane domains from CD2, CD3d, CD3g, CD3z, CD4, CD8A, CD8B, CD22, CD27, CD28, CD40, CD79a, CD79b, CD80, CD84, CD86, CD137, CD244, CRACC, CRTAM, CLTA-4, MHC-I, MHC-II, platelet-derived growth factor receptor, FCGR1A, FCGR2A, FCG2B, FCGR3A, FCRL1, FCRL2, FCRL3, FCRL4, FCRL5, FCRL6, KIR2DL1, KIR2DL2, KIR2DL3, KIR2DL4, KIR2DL5A, KIR2DL5B, KIR3DL1, KIR3DL2, KIR3DL3, LAG3, GITR, OX40, PD-1, PD-L1, PD-L2, TLR, SLAMF, LILRB1, LILRB2, NKG2A, NKG2C, NKG2D, TIGIT, IgG, IgM, IgA, IgE, IgD, or immunoglobulin. A repertoire of antigen/ligands can be made and engineered into the antigen/ligand presenting cell. Optionally, variation in the antigen/ligand library can be made by introducing genetic mutations into desired locations (e.g., randomly, or site specific) on the antigen/ligand of interest. Genetic mutations can be substitution, deletion, insertion, and rearrangement of DNA fragments. Specific genetic mutations of choice can be generated randomly, enriched in the region of interest (e.g. interacting domains of the ligand), or recommended by a computational algorithm. Examples of computational algorithms to recommend genetic mutation strategies include protein structure analysis, computational docking, molecular dynamics simulation, regression, statistics-based classifier, random forest, support vector machine, and neural networks.

Antigen libraries can be made as fusions of antigen polypeptides with an appropriate MHC molecule or two separate molecules of a peptide and MHC. Algorithms can be used for identifying presentable antigens including, for example, those disclosed in Chen et al., Nature Biotechnology 37:1332-43 (2019), Jurtz et al., J. Immunol. 199:3360-68 (2017), and Abelin et al., Immunity 51:766-79 (2019), all of which are incorporated by reference in their entirety for all purposes. The nucleic acid encoding the antigen-MHC fusions can optionally include a barcode that identifies the antigen polypeptide of the fusion. The library of antigen-MHC molecule fusions is placed into an appropriate host cell that will display the antigen-MHC molecule complex fused or unfused, as well as the barcode, on its surface (e.g., a cell line such as K562). This barcode can be DNA or RNA and either attached to cell membrane directly, the MHC molecule, or attached to another protein (e.g., GFP) that when expressed will transport the barcode to the cell surface. The host cells for the antigen library can also include a reporter (e.g., the cells can be engineered to express membrane GFP).

The repertoire of TCR-Fc fusions in the monocyte cells can be mixed with the library of antigen::MHC fusion proteins. Macrophage cells with TCR antigen binding domains that can bind the antigen polypeptides displayed on the MHC can phagocytose the cell displaying the antigen-MHC fusion that binds to the TCR of the TCR-Fc chimeric receptor. If the cells displaying the antigen-MHC fusion include a reporter, the signal from the reporter can be used to separate TCR-Fc cells that have phagocytosed an antigen-MHC fusion displaying cell. For example, if the reporter is an optical reporter that optical reporter can be used to separate TCR-Fc cells that have phagocytosed an antigen-MHC using FACs sorting. Optionally, the phagocytosing cell type can include a reporter (e.g., an optical reporter different from the antigen presenting cell reporter). When both the cells with the chimeric TCR repertoire and the cells with the antigen library have different optical reporters, FACs sorting can be used to select cells that have both optical signals (e.g., by first selecting cells with one of the optical signals and then selecting cells with the other optical signal).

Alternatively, the repertoire of engineered receptor cells (e.g., monocytes with TCRs) can be mixed with the library of ligands (e.g., antigen-MHC fusion proteins). Receptor cells interact with and activate against cells displaying the ligand (e.g., antigen-MHC complex fused or unfused) that binds to the receptor (e.g., TCR) of the engineered cell (e.g., monocyte or macrophage). Receptor cells capture fragments of the membrane of the ligand cells through trogocytosis, including DNA or RNA barcodes on the cell surface (identifying the ligand). If the cells displaying the ligand (e.g., antigen-MHC fusion) include a membrane bound reporter or a dye, the signal from the membrane bound reporter can be used to separate engineered receptor cells that have interacted with ligand displaying cell (e.g., an antigen-MHC fusion displaying cell) from other cells. For example, if the reporter is an optical reporter that optical reporter can be used to separate receptor-cells that have activated against a ligand (e.g., an antigen-MHC) using FACs sorting. Optionally, the trogocytosing cell type can include a reporter (e.g., an optical reporter different from the antigen presenting cell reporter). When both the engineered receptor-cells and the cells with the ligand library have different optical reporters, FACs sorting can be used to select cells that have both optical signals (e.g., by first selecting cells with one of the optical signals and then selecting cells with the other optical signal).

The engineered receptor-cells cells that have activated against a ligand (e.g., an antigen-MHC) can be separated for bulk sequencing or single cell sequencing to identify the antigen polypeptide and the receptor (e.g., TCR variable region) that have formed the receptor-ligand pair. Either the barcodes of the receptor and ligand can be sequenced to identify the receptor and the ligand, or the nucleic acids encoding the receptor (e.g., TCR variable region) and the receptor (e.g., antigen) can be directly sequenced to identify the receptor and ligand.

A library of engineered receptors (e.g., T-cell receptors or T-cell receptor mimics) can represent up to $10^3$, $10^4$, $10^5$, $10^6$, $10^7$, $10^8$, $10^9$, or $10^{10}$ different receptors (e.g., T-cell receptors). The library of ligands (e.g., antigen-MHC fusions can represent $10^3$ or $10^4$ or $10^5$ or $10^6$ or $10^7$ or $10^8$ or $10^9$ or $10^{10}$ different ligands (e.g., antigen-MHC fusions). Bar Coded Receptor Repertoires The receptor repertoire can be obtained starting from the nucleic acids encoding the receptor of interest from the appropriate cell type (e.g., the receptors disclosed for T-cells, B-cells, NK cells, macrophages and/or neutrophils above). For example, a T-cell receptor repertoire can be obtained from one or more of CD8+ T-cells, CD4+ T-cells, regulatory T-cells, memory T-cells, helper T-cells, or cytotoxic T-cells. The T-cells may be naïve or include effector and/or memory T-cells that have been exposed to antigens of interest or other antigens. Memory T-cells may be stem cell memory cells $T_{SCM}$), central memory cells ($T_{CM}$), transitional memory cells ($T_{TM}$), and/or effector memory cells ($T_{EM}$). The T-cells may be $Th_1$, $Th_2$, $Th_9$, $Th_{17}$, $Th_{22}$, $T_{reg}$, $T_{fh}$ and Cytotoxic T lymphocytes (CTL). T-cell receptors can be obtained from either (or both) the genomic DNA of the T-cells (or subpopulation of T-cells) and/or the mRNA of the T-cells (or subpopulation of T-cells). Repertoires of T-cell receptors can be obtained using techniques and primers well known in the art and described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. T-cell receptors polypeptides can be used as separate chains to form the TCR. Alternatively, the T-cell receptors polypeptide chains can be converted to single chain TCRs. Single chain T-cell receptors can be made from nucleic acids encoding human alpha and human beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/Aggen_David.pdf?sequence=1, all of which are incorporated by reference in their entirety for all purposes.

Immune cells (e.g., T-cells) can be obtained from a number of sources, including peripheral blood mononuclear cells, bone marrow, lymph node tissue, spleen tissue, embryos, and tumors. Immune cells (e.g., T cells) can be obtained from a unit of blood collected from a subject using any number of techniques known to a person of ordinary skill, such as Ficoll separation. Immune cells (e.g., T-cells) from the circulating blood of an individual can be obtained by apheresis or leukapheresis. Genomic DNA or mRNA/cDNA can be used to obtain the nucleic acids encoding the receptors (e.g., T-cell receptors).

T cells that have infiltrated a tumor can be used as the source of the T-cell repertoire. T-cells may be removed during surgery. T cells may be isolated after removal of tumor tissue by biopsy. T cells may be isolated from a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

Enrichment of a T cell population by negative selection can be accomplished with a combination of antibodies directed to surface markers unique to the negatively selected cells. A preferred method is cell soiling and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

T cells may also be antigen-specific T cells. For example, tumor-specific T cells can be used. Antigen-specific T cells can be isolated from a patient of interest, such as a patient afflicted with a cancer or an infectious disease. Antigen-specific T cells can be induced by vaccination of a subject with a particular antigen, either alone or in conjunction with an adjuvant or pulsed on dendritic cells. Antigen-specific cells for use in expansion may also be generated in vitro using any number of methods known to person of ordinary skill.

Each T-cell receptor is made with two protein chains: an alpha chain and a beta chain, or a gamma chain and a delta chain. Each chain has two extracellular domains: a variable (V) region and a constant (C) region. The constant region is proximal to the cell membrane, followed by a transmembrane region and a short cytoplasmic tail, while the variable region binds to the antigen:MHC complex. The variable domain of both the TCR alpha-chain and beta-chain each have three hypervariable or complementarity determining regions (CDRs). There is also an additional area of hypervariability on the beta-chain (HV4) that does not normally contact antigen and, therefore, is not considered a CDR. CDR3 is the main CDR responsible for recognizing processed antigen, although CDR1 of the alpha chain has also been shown to interact with the N-terminal part of the antigenic peptide, whereas CDR1 of the beta-chain interacts with the C-terminal part of the peptide. CDR2 recognizes the MHC. CDR4 of the beta-chain is not thought to participate in antigen recognition, but has been shown to interact with superantigens. The constant domain of the TCR consists of short connecting sequences in which a cysteine residue forms disulfide bonds, which form a link between the two chains.

A form of TCR mimics includes chimeric T-cell receptors or chimeric antigen receptors (CAR). Chimeric T-cell receptors are made by fusing appropriate cytoplasmic regions with single chain TCRs or with one of the chains of a T-cell receptor. Single chain T-cell receptors can be made according to Zhang et al., Cancer Gene Therapy 11:487-496 (2004), which is incorporated by reference in its entirety for all purposes. Appropriate cytoplasmic regions include one or more of an Fc cytoplasmic domain, CD3ζ, CD28, B7.1, CD137, CD19 intracellular activation domain, CD64 intracellular activation domain, CD32 intracellular activation domain, CD16 intracellular activation domain, CD23 intracellular activation domain, or Lck activation domain. Costimulatory domains that can be used in the chimeric TCR include, for example, CD3ζ, CD28, B7.1, CD137, CD19 intracellular activation domain, CD64 intracellular activation domain, CD32 intracellular activation domain, CD16 intracellular activation domain, CD23 intracellular activation domain, Lck activation domain, CD27, OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, MyD88, and the like. A chimeric T-cell receptor fused with a Fc signaling domain and optionally one or more costimulatory domains can cause a monocyte/macrophage to phagocytose in response to ligand binding to the TCR. Alternatively, A chimeric T-cell receptor or chimeric antigen receptor with a signaling domain and optionally one or more costimulatory domains can cause trogocytosis in response to antigen interacting with the receptor.

Optionally T-cells contain TCR barcodes attached to their cell membrane via membrane bound DNA or RNA binding proteins. Antigen barcodes of antigen presentation cells can be introduced simultaneously or sequentially with the antigen coding cDNA or mRNA. Membrane bound nucleic acid (DNA or RNA) binding proteins can be engineered from zinc finger nuclease, transcription factor binding protein, replication protein A, CRISPR Cas9, Cas13, Cpf1, phage RNA binding proteins, bacterial single strand binding protein, or engineered restriction digestion enzymes. The nucleic acid binding proteins have binding motifs and these are set out for an exemplary set of proteins in Table 1.

on the cytoplasmic side of the membrane. Barcodes can be the CDRs of a TCR or a unique sequence of the antigen, or

TABLE 1

Binding Motifs for Nucleic Acid Binding Proteins

| Binding protein | Target nucleotide type | Example target sequence motifs |
|---|---|---|
| Transcription factor TCF21 | DNA | CAGCTGTTG |
| Transcription factor MYCN | DNA | CCACGTG |
| Transcription factor CEBPA | DNA | ATTGCACAATA (SEQ ID NO: 1) |
| Replication protein A | DNA | Most of single stranded DNA |
| SpCas9 | DNA | Depending on guide RNA with NGG motif |
| SaCas9 | DNA | Depending on guide RNA with NGRRT or NGRRN motifs |
| Cpf1/Cas12a | DNA | Depending on guide RNA with TTTV motif |
| Zinc finger sZF1 | DNA | GTCGGGGTA |
| Zinc finger sZF2 | DNA | GAAGCAGCA |
| Zinc finger sZF3 | DNA | GTGGCGGAT |
| Zinc finger sZF13 | DNA | GACGCTGCT |
| Lamda BoxB RNA binding protein | RNA | GGGCCCUGAAGAAGGGCCC (SEQ ID NO: 2) or its variants |
| P22 BoxB RNA binding protein | RNA | UGCGCUGACAAAGCGCG (SEQ ID NO: 3 or its variants |
| MS2 RNA binding protein | RNA | ACAUGAGGAUUACCCAUGU (SEQ ID NO: 4) or its variants |
| MS2 RNA binding protein | RNA | AGUUCAGCAUUAGCGAACU (SEQ ID NO: 5) or its variants |

Note:
V = A, C, G;
N = A, T, C, G;
R = A, G

The Membrane bound nucleic acid binding protein can be engineered from a nucleic acid binding protein engineered (if needed) with a synthetic transmembrane domain. Exemplary synthetic transmembrane domains include wildtype or modified transmembrane domains from CD2, CD3d, CD3g, CD3z, CD4, CD8A, CD8B, CD22, CD27, CD28, CD40, CD79a, CD79b, CD80, CD84, CD86, CD137, CD244, CRACC, CRTAM, CLTA-4, MHC-I, MHC-II, platelet-derived growth factor receptor, FCGR1A, FCGR2A, FCG2B, FCGR3A, FCRL1, FCRL2, FCRL3, FCRL4, FCRL5, FCRL6, KIR2DL1, KIR2DL2, KIR2DL3, KIR2DL4, KIR2DL5A, KIR2DL5B, KIR3DL1, KIR3DL2, KIR3DL3, LAG3, GITR, OX40, PD-1, PD-L1, PD-L2, TLR, SLAMF, LILRB1, LILRB2, NKG2A, NKG2C, NKG2D, TIGIT, IgG, IgM, IgA, IgE, IgD, or immunoglobulin. The nucleic acid binding domain can be engineered to be present on the cytoplasmic side of the membrane using engineering techniques known in the art. For example, many of the synthetic transmembrane domains have the c-terminus of the polypeptide chain on the cytoplasmic side of the membrane. Thus, the nucleic acid binding protein can be engineering into the c-terminus end of the synthetic transmembrane domain so the nucleic acid binding protein portion is present a barcode can be introduced in the nucleic acid encoding the receptor or antigen or ligand so that the mRNA expressed includes the barcode. The nucleic acid encoding the receptor/antigen/ligand can also be engineered to include the binding motif for the membrane bound nucleic acid binding protein so that the mRNA expressed includes the binding motif. This will result in mRNA for the receptor or antigen being bound to the membrane bound nucleic acid binding protein. When trogocytosis occurs between the receptor cell and the ligand presenting cell, membrane bound nucleic acid binding protein with the barcode will also be transferred resulting in both cells having membrane bound barcodes for the receptor (e.g., TCR or CAR) and the ligand (e.g., antigen).

A repertoire of chimeric TCRs can have $10^3$, $10^4$, $10^5$, $10^6$, $10^7$, $10^8$, $10^9$, or $10^{10}$ different TCRs. The repertoire of chimeric TCRs can represent the population of TCRs found in the genomic DNA of a subject, or of naïve T-cells, or of T-cells from a subject that has mounted an immune response to an antigen of interest, or from any of the populations of T-cells described above. A suitable cell type for the repertoire of chimeric TCRs are monocytes of macrophages including, for example, THP-1 cells.

Barcoded Antigen/Ligand Repertoires

A ligand library is made from desired ligands (e.g., antigens). HLA gene and antigen sequences can be fused into a single peptide or encoded as separate peptides. HLA alpha and beta chains can be fused or encoded as separate peptides. Antigen sequences are 8-25 amino acids long, as HLA can only bind and present a fragment of a full protein. A computer algorithm can be used to select peptides to use as presentable antigens, suitable methods of identifying presentable peptide antigens are described in Chen et al., Nature Biotechnol. 37:1332-43 (2019), Jurtz et al., J. Immunol. 199:3360-68 (2017). Abelin et al., J. Thero. Biol. 389:214-224 (2016), all of which are incorporated by reference in their entirety for all purposes.

T-cell receptors can recognize antigens bound to major histocompatibility complex (MHC) molecules. MHC molecules include class I, class II, and class III. Both class I and class II MHC molecules play a role in immune responses. MHC molecules of class I consist of a heavy chain and a light chain and are capable of binding a peptide of about 8 to 11 amino acids, but usually 9 or 10 amino acids, and presenting it to naive and cytotoxic T-lymphocytes. The peptide bound by the MHC molecules of class I can originate from an endogenous protein antigen. The alpha chain of the MHC molecules of class I can be an HLA-A, HLA-B or HLA-C monomer, and the beta chain can be a beta-2-microglobulin.

MHC molecules of class II consist of an alpha-chain and a beta-chain and are capable of binding a peptide of about 8 to 24 amino acids and present it to T-cells. The peptide bound by the MHC class II molecule can originate from an extracellular or exogenous protein antigen. The alpha-chain and the beta-chain can be HLA-DR, HLA-DQ and HLA-DP monomers. MHC class II can be expressed by all cell types, but normally occurs on professional antigen-presenting cells (APCs): macrophages, B cells, and especially dendritic cells. An APC takes up an antigenic protein, performs antigen processing, and returns a molecular fraction of it—a fraction termed the epitope—and displays it on the APC's surface coupled within an MHC class II molecule (antigen presentation). On the cell's surface, the epitope can be recognized by immunologic structures like T-cell receptors (TCRs).

Optionally antigen presenting cells contain antigen barcodes attached to their cell membrane via membrane bound DNA or RNA binding proteins. Antigen barcodes of antigen presentation cells can be introduced simultaneously or sequentially with the antigen coding cDNA or mRNA. Membrane bound DNA or RNA binding proteins can be engineered zinc finger nuclease, transcription factor binding protein, replication protein A, CRSIPR Cas9, Cas13, Cpf1, phage RNA binding proteins, bacterial single strand binding protein, or engineered restriction digestion enzymes. Membrane bound antigen barcode enable information transfer between APCs and T-cells upon trogocytosis.

MHC-antigen complexes can be linked together in one or a combination of any of the following ways for creating antigen libraries: genetically linking MHC alpha chain, MHC beta chain, and antigen encoding sequence with flexible linker (e.g. GCGGSGGGGSGGGGS), genetically linking MHC genes with self-cleaving peptide sequences (e.g. T2A, P2A, or F2A), or overexpression of antigen peptides in a cell line with desired MHC alleles. Antigen DNA or RNA can be recovered through bulk or single-cell sequencing of APCs in the library, serving as a natural barcode. Antigen DNA/RNA barcode (antigen sequences) can be amplified using PCR and primers targeting antigen flanking regions. After phagocytosis where an APC is consumed by a macrophage, allowing paired antigen and TCR data to be recovered from one cell (the macrophage that has "eaten" the APC) via DNA or RNA sequencing. Alternatively, after T-cell activation and trogocytosis where an APC and a T-cell exchanged membrane pieces, barcodes (either DNA or RNA) allowing paired antigen and TCR data to be recovered from one cell (APC or T-cell contains both antigen and TCR barcodes) via DNA or RNA sequencing. Methods for making single chain MHC molecules with an antigen peptide are described in, for example, Mottez et al., Cells expressing a major histocompatibility complex class I molecule with a single covalently bound peptide are highly immunogenic, J. Exp. Med. 181:493-502 (1995); Ignatowicz et al., Cell surface expression of class II MHC proteins bound by a single peptide, J. Immunol. 154:3852-3862 (1995); Uger et al., Creating CTL targets with epitope-linked B2 microglobulin constructs, J. Immunol. 160:1598-1605 (1998); Yu et al., Cutting edge: single-chain trimers of MHC class I molecules form stable structures that potently stimulate antigen-specific T cells and B cells, J. Immunol. 168: 3145-3149 (2002); Hansen et al., Translational and basic applications of peptide-MHCI single chain trimers, Trends Immunol 31:363-369 (2010); Kotsiou et al., Properties and applications of single-chain major histocompatibility complex class I molecules, Antioxidants Redox Signaling 15:645-655 (2011); Zhao et al., Use of single chain MHC technology to investigate co-agonism in human CD8+ T cell activation, J. Vis. Exp. 144:e59126 (2019), all of which are incorporated by reference in their entirety for all purposes. Alternatively, the MHC chains (class I or II) are recombinantly made separately and assembled in the recombinant cell to form an MHC molecule. Antigens can be co-expressed in the cell as peptides for combination with the MHC molecules, or as whole antigen protein to be processed in degradation into peptides that can be displayed on the MHC molecules. Methods for expressing antigen::MHC complexes in this way are described in, for example, Stevens et al., Efficient generation of major histocompatibility complex class I peptide complexes using synthetic peptide libraries, J. Bio. Chem. 273:2874-2884 (1998); Braendstrup et al., MHC class II tetramers from isolated recombinant alpha and beta chains refolded with affinity tagged peptides, PLoS ONE 8:E73648 (2013); Saini et al., Empty peptide receptive MHC class I molecules for efficient detection of antigen specific T cells, Sci. Immunol. 4:eaau9039 (2019).

Infectious disease antigens that can be used in the antigen library include antigens from an infectious agent. The infectious agent can be a bacterial pathogen or a viral pathogen. Bacterial pathogens include, for example, a bacterial strain of *Staphylococci, Streptococcus, Escherichia coli, Pseudomonas, Salmonella, Staphylococcus aureus, Neisseria gonorrhoeae, Streptococcus pyogenes*, Group A *Streptococcus*, Group B *Streptococcus* (*Streptococcus agalactiae*), *Streptococcus pneumoniae, Clostridium tetani, Helicobacter pyloris, Legionella pneumophilia*, a bacterial strain of *Mycobacteria* sps. (e.g. *M. tuberculosis, M. avium, M. intracellulare, M. kansaii,* or *M. gordonea*), *Neisseria meningitides, Listeria monocytogenes, R. rickettsia, Salmonella* spp., *Brucella* spp., *Shigella* spp., certain *E. coli* strains or other bacteria that have acquired genes with invasive factors, and any of the foregoing or other bacteria that have acquired antibiotic resistance factors.

Viral pathogens include, for example, Ebola, Zika, RSV, Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), hepatitis C virus, Epstein-Barr, or Kaposi's sarcoma viruses.

The antigen library can include either tumor associated antigens, tumor neoantigens, or other antigens found preferentially on cancer cells. Tumor associated antigens that can be used in the antigen library include any over- or aberrantly expressed genes or proteins in tumor cells, for example, mesothelin, disialoganglioside (GD2), Her-2, MUC1, GPC3, EGFRVIII, CEA, CD19, EGFR, PSMA, GPC2, folate receptor β, IgG Fc receptor, PSCA, PD-L1, EPCAM, Lewis Y Antigen, L1CAM, FOLR, CD30, CD20, EPHA2, PD-1, C-MET, ROR1, CLDN18.2, NKG2D, CD133, TSHR, CD70, ERBB, AXL, Death Receptor 5, VEGFR-2, CD123, CD80, CD86, TSHR, ROR2, CD147, kappa IGG, IL-13, MUC16, IL-13R, NY-ESO-1, IL13RA2, DLL3, FAP, LMP1, TSHR, BCMA, NECTIN-4, MG7, AFP (alpha-fetoprotein), GP100, B7-H3, Nectin-4, MAGE-A1, MAGE-A4, MART-1, HBV, MAGE-A3, TAA, GP100, Thyroglobulin, EBV, HPV E6, PRAME, HERV-E, WT1, GRAS G12V, p53, TRAIL, MAGE-A10, HPV-E7, KRAS G12D, MAGE-A6, CD19, BCMA, CD22, CD123, CD20, CD30, CD33, CD138, CD38, CD7, SLAMF7, IGG FC, MUC1, Lewis Y Antigen, CD133, ROR1, FLT3, NKG2D, Kappa light chain, CD34, CLL-1, TSLP, CD10, PD-L1, CD44V6, EBV, CD5, GPC3, CD56, integrin B7, CD70, MUCL, CKIT, CLDN18.2, TRBC1, TAC1, CD56, CD4, CD2, CD18, CD27, CD37, CD72, CD79A, CD79B, CD83, CD117, CD172, ERBB3, ERBB4, DR5, HER2, CS1, IL-1RAP, ITGB7, SLC2A14, SLC4A1, SLC6A11, SLC7A3, SLC13A5, SLC19A1, SLC22A12, SLC34A1, slc45A3, SLC46A2, Fra, IL-13Ra2, ULBP3, ULBP1, CLD18, NANOG, CEACAM8, TSPAN16, GLRB, DYRK4, SV2C, SIGLEC8, RBMXL3, HIST1HIT, CCR8, CCNB3, ALPPL2, ZP2, OTUB2, LILRA4, GRM2, PGG1, NBIF3, GYPA, ALPP, SPATA19, FCRLI, FCRLA, CACNG3, UPK3B, 12UMO4, MUC12, HEPACAM, BPI, ATP6V0A4, HMMR, UPK1A, ADGRV1, HERC5, C3AR1, FASLG, NGB, CELSR3, CD3G, CEACAM3, TNFRSFBC, MS4AB, S1PR5, EDNRB, SCN3A, ABCC8, ABCB1, ANO1, KCND2, HTR4, CACNB4, HTR4, CNR2, 26LRB, EXOC1, ENTPP1, ICAM3, ABCGB, SCN4B, SPN, CD68, ITGAL, ITGAM, SCTR, CYYR1, CLCN2, SLARA3, and JAG3. Tumor neoantigens that can be used in the antigen library include any mutated genes or proteins unique to or enriched on tumor cells, for example, ACVR2A K435fs, AKT1 E17K, AR Q58L, ASXL1 G610, ATR K771fs, BRAF V600E, CHEK2 K416E, CRIPAK R154fs, CTNNB1 S26F, CTNNB1 S30C, CTNNB1 D25N, CTNNB1 G27R, CTNNB1 S26C, CTNNB1 S30F, DNMT3A R882H, DNMT3A R882C, EGFR A244V, EGFR G553V, EGFR A244T, EGFR R177C, EGFR L813R, EP300 D1399N, FBXW7 R465H, FBXW7 R505G, FBXW7 R505C, FBXW7 R465C, FGFR2 N550K, FGFR2 S252W, FGFR3 S249C, FLT3 D835Y, GATA3 P409fs, IDH1 R132C, IDH1 R132H, IDH2 R88Q, KRAS G12V, KRAS G13D, KRAS G12D, KRAS G12C, KRAS A146T, KRAS G12A, KRAS Q61L, MTOR S2215Y, NFE2L2 R18G, NFE2L2 E63Q, NFE2L2 D13H, NPM1 W288fs, NRAS G13D, NRAS Q61R, NRAS G12D, NRAS Q61K, NRAS Q61L, PIK3CA E453K, PIK3CA E545A, PIK3CA M1043I, PIK3CA M1043V, PIK3CA R108H, PIK3CA H1047R, PIK3CA Q546K, PIK3CA G118D, PIK3CA N345K, PIK3CA H1047L, PIK3CA R88Q, PIK3CA K111E, PIK3CA Q546R, PIK3CA Q546P, PIK3CA E726K, PIK3CA E542K, PIK3CA E81K, PIK3CA E545K, PIK3CA C420R, PIK3CA R93Q, PPP2R1A P99R, PPP2R1A R103W, PTEN A328fs, PTEN R130Q, PTEN R130G, PTEN T319fs, RPL22 K15fs, SF3B1 K700E, SMAD4 R361H, TGFBR2 E150fs, TP53 R249M, TP53 E285K, TP53 R249S, TP53 G266V, TP53 R158H, TP53 C141Y, TP53 Y236C, TP53 V173M, TP53 S241F, TP53 V173L, TP53 E271K, TP53 E286K, TP53 C275Y, TP53 R110L, TP53 R273L, TP53 H179Y, TP53 V216M, TP53 V157F, TP53 H193R, TP53 T125, TP53 I195T, TP53 H179R, TP53 G245S, TP53 R282W, TP53 R273C, TP53 Y220C, TP53 R248W, TP53 R248Q, TP53 R273H, TP53 R175H, TP53 Y205C, TP53 M237I, TP53 C238F, TP53 V272M, TP53 C242F, TP53 L194R, TP53 A159V, TP53 G245D, TP53 H193L, TP53 Y163C, TP53 R158L, TP53 G108fs, TP53 G245V, TP53 C238Y, TP53 C176F, TP53 Y234C, TP53 C176Y, TP53 K132N, U2AF1 S34F, VHL L89H, VHL S111N, VHL W117fs. Tumor neoantigens can be generated by single nucleotide mutation, frameshift mutation, insertion, deletion, alternative splicing, or extrachromosomal circular DNA.

Suitable antigens for the library include KRAS variants which are tumor neoantigens often found in pancreatic cancer, lung cancers, colon cancers, and bile duct cancers. Table 2 below shows common KRAS mutations associated with certain cancers.

TABLE 2

| KRAS Mutations | | |
| --- | --- | --- |
| KRAS Mutation | Frequency of Mutation | Cancer Type |
| G12D | 25-50% | Pancreatic cancer |
| G12V | 34% | Pancreatic cancer |
| G12H | 16% | Pancreatic cancer |
| G12V | 20-40% | Ovarian cancer, Pancreatic cancer |
| G12C | 3-38% | Lung adenocarcinoma |
| G12A | 3-13% | Endometrial cancer |
| G12S | 2-13% | Cholangiocarcinoma |
| G12R | 1-13% | Pancreatic cancer |
| G13D | 4-14% | Colon Cancer |

These KRAS mutant alleles can be used in an antigen library to screen for TCRs that can bind to the mutant allele and not the wild-type allele. Such discriminating TCRs can be used to target immunotherapy at cancers with these KRAS mutations.

A suitable cell type for the antigen library is an antigen presenting cell. The APC can lack MHC molecules on its surface. A suitable antigen presenting cell includes, for example, K562 cells.

Also described herein are retrovirus-based systems that repurpose viral tropism as a method of selecting for molecular interactions and replace the binding functions of wild-type virus surface proteins with those of the antigen/ligand of interest, for example, by encoding these antigens/ligand variants on the corresponding transfer plasmid used to make the virus, thereby ensuring that the resulting virus displays the antigen/ligand variant on its surface and packaging the corresponding genetic sequence. As such, when the virus enters a target cell (e.g., bearing a receptor that binds the displayed extracellular targeting domain of the antigen/ligand variant), cell entry results in integration of the genetic sequence of the displayed protein into the genome of the target cell at a desired location.

The retrovirus can have a nucleic acid encoding a structure: S-ETD-LGD-IRES-R, wherein S encodes a signal sequence, ETD encodes an extracellular targeting domain; LGD encodes the antigen/ligand, IRES encodes an internal ribosome entry site, and R encodes a reporter (e.g., a fluorescent protein or selection marker such as antibiotic resistance). The IRES and R are optional, and the nucleic acid can encode S-ETD-LGD. The retrovirus also encodes a mutated viral envelope protein comprising at least one mutation that diminishes its native entrance function. IRES sequences can be substituted by a 2A self-cleaving peptide sequence (T2A, P2A, F2A, and E2A) which similarly allows co-expression of two genes with one promoter.

Described herein are retroviruses comprising a viral envelope protein having at least one mutation that diminishes its native function, a non-viral membrane-bound protein comprising a membrane-bound domain, an extracellular antigen/ligand domain, and a nucleic acid encoding a reporter. The retrovirus disclosed herein can have one or more elements derived from a retroviral genome (naturally-occurring or modified) of a suitable species. Retroviruses include 7 families: alpharetrovirus (Avian leucosis virus), betaretrovirus (Mouse mammary tumor virus), gammaretrovirus (Murine leukemia virus), deltaretrovirus (Bovine leukemia virus), epsilonretrovirus (Walleye dermal sarcoma virus), lentivirus (Human immunodeficiency virus 1), and spumavirus (Human spumavirus). Other examples of retroviruses are provided in U.S. Pat. No. 7,901,671, which is incorporated by reference in its entirety for all purposes.

Modified lentiviral genomes can be useful as viral vectors for the delivery of a nucleic acids to a host cell. Host cells can be transfected with lentiviral vectors, and optionally additional vectors for expressing lentiviral packaging proteins (e.g., VSV-G, Rev, and Gag/Pol) to produce lentiviral particles in the culture medium. Non-limiting examples of retrovirus constructs useful herein include, for example, lentiviral vectors, human immunodeficiency viral (HIV) vector, avian leucosis viral (ALV) vector, murine leukemia viral (MLV) vector, murine mammary tumor viral (MMTV) vector, murine stem cell virus, and human T cell leukemia viral (HTLV) vector. These retrovirus constructs comprise proviral sequences from the corresponding retrovirus.

The retroviral vectors described herein may further comprise additional functional elements as known in the art to address safety concerns and/or to improve vector functions, such as packaging efficiency and/or viral titer. Additional information may be found in US20150316511, WO2015/117027, and WO2019/056015, each of which are incorporated by reference in their entirety for all purposes.

The viral envelope protein can be any viral envelope protein of any retrovirus (e.g., lentivirus). A viral envelope protein may be a VSV-G envelope protein, a measles virus envelope protein, a nipah virus envelope protein, or a cocal virus G protein. The native function that is diminished by a mutation of a viral envelope protein can be viral tropism (e.g., ability to infect cells, bind to cells, etc.) For example, a mutated VSV-G envelope protein can be mutated at amino acid H8, K47, Y209, and/or R354. A mutated VSV-G envelope protein can have one or more of the following changes H8A, K47A, K47Q, Y209A, R354A, and/or R354Q. Exemplary mutated VSV-G envelope proteins are described in Nikolic et al., "Structural basis for the recognition of LDL-receptor family members by VSV glycoprotein." Nature Comm., 2018, 9:1029, which is incorporated by reference in its entirety for all purposes. A mutated measles virus envelope protein can have mutation(s) at Y481, R533, S548, and/or F549. A mutated measles virus envelope protein can have one or more of Y481A, R533A, S548L, and/or F549S. A mutated Nipah virus envelope protein can have mutation(s) at E501, W504, Q530, and/or E533. A mutated measles virus envelope protein can have one or more of E501A, W504A, Q530A, and/or E533A. A mutated cocal virus G protein can have mutation(s) at K64 and/or R371. A mutated cocal virus G protein can one or more of K64Q and/or R371A.

A membrane-bound domain is a protein or peptide that has an amino acid sequence that enables the protein or peptide to be fully or partially embedded or associated with the membrane (e.g., envelope) of the retrovirus. A membrane-bound domain can enable presentation and delivery of the extracellular antigen/ligand domain to the extracellular environment. A membrane-bound domain can have an intracellular domain, a transmembrane domain, and an extracellular domain. The membrane-bound domain can be a Major Histocompatibility Complex (MHC) protein or fragment thereof. A MHC protein may be a Class I or Class II MHC protein.

The retroviruses present in a library of retroviruses can collectively comprise a library of different antigen/ligands fused to the membrane-bound domain. The extracellular antigen/ligand is capable of binding to a target cell. The extracellular antigen/ligand domain can bind to a protein or receptor ligand (e.g., a T-cell receptor) that is present on the cell surface of a cell or a subset of a population of cells. The ligand-extracellular antigen/ligand domain binds to a receptor that is present on the cell surface of a T cell or a subset of a population of T cells. This binding interaction between an extracellular antigen/ligand domain of a retrovirus and a receptor, protein or ligand of a cell enables the retrovirus to enter the cell (e.g., an antigen-specific cell, e.g., a T cell).

The non-viral membrane-bound protein can include a linker positioned between the membrane-bound domain and the extracellular antigen/ligand domain. A linker can be an amino acid linker and may be a rigid linker, a flexible linker, or an oligomerized linker. A rigid linker can be an amino acid sequence that lacks flexibility (e.g., may comprise at least one proline). For example, a rigid linker can be derived from a platelet-derived growth factor receptor (PDGFR) stalk or a CD8-alpha stalk. A flexible linker is an amino acid sequence that has many degrees of freedom (e.g., may comprise a plurality of amino acids with small side chains, e.g., glycine or alanine). An oligomerized linker is an amino acid that can oligomerize to another related amino acid. An oligomerized linker can be an amino acid sequence that can form a dimer, trimer, or tetramer. For example, an oligomerized linker can be made from an IgG4 hinge domain.

The description also relates to libraries of retroviruses, wherein a library comprises a plurality of unique retroviruses, wherein each unique retrovirus comprises a viral envelope protein comprising at least one mutation that diminishes its native function, a non-viral membrane-bound protein comprising a membrane-bound domain and an extracellular targeting domain, and optionally a nucleic acid encoding a reporter, and wherein each unique retrovirus comprises a different and unique extracellular targeting domain. Also described herein are libraries of cells comprising retroviruses, wherein a library comprises a plurality of unique cells, wherein each unique cell comprises a unique retrovirus.

Libraries can include a plurality of retroviruses with nucleic acids encoding different MHC-peptide fusions for use in screening populations of T cells. In such libraries, the MHC-peptide fusion displayed on the virus surface will enable T cell infection in a TCR-specific manner. Infected T cells can be collected and sequenced, allowing for the identification of MHC-peptide ligands that can infect a subset of a T cell population of interest and the ability to simultaneously track TCR sequences and reactive MHC-peptide ligands. The MHC-peptide retroviral libraries can comprise randomized transfer vectors containing randomized MHC-peptide targeting elements. The randomly derived libraries can be generated using degenerate oligonucleotide primers. The targeted libraries can be specific for a unique set of antigens (e.g., all possible viral or bacterial antigens for a particular target of interest—human immunodeficiency virus, tuberculosis TB, etc.; or all possible neoantigens for a particular subject). Antigen/Ligand sequences can be chosen to maximize their chance to interact with the receptors or binding proteins. Variation in the antigen/ligand library can be made by introducing genetic mutations into desired locations (e.g., randomly, or site specific) on the antigen/ligand of interest. Genetic mutations can be substitution, deletion, insertion, and rearrangement of DNA fragments. Specific genetic mutations of choice can be generated randomly, enriched in a region of interest (e.g., interacting domains of the ligand), or recommended by a computational algorithm. Examples of computational algorithms for genetic mutation strategies include protein structure analysis, computational docking, molecular dynamics simulation, regression, statistics-based classifier, random forest, support vector machine, and neural networks.

Barcode sequences can be randomly generated nucleotide sequences of any length above 4. For example, a 15 nucleotide DNA sequence can provide a diversity of $4^{15}=1$ $e^9$. Barcode sequences can be amino acid encoding or purely functioning as marker sequences. For example, one design of retroviral plasmid contains two cloning site: one for antigen encoding sequence, and one for barcode sequence.

After inserting both barcode and ligand sequences into the viral plasmid and amplifying viral plasmids either via PCR or *E. coli* amplification, a fraction of plasmids can be sequenced via bulk sequencing. As barcode and ligand sequences are near each other, bulk sequencing data can establish one to one mapping between barcode sequence and ligand sequence.

Host Cells

Nucleic acids encoding a polypeptide described herein (e.g., a TCR or an antigen) are cloned into an appropriate expression vector for expression of the polypeptide in a host cell. Host cells can be mammalian cells, such as mouse, rat, rabbit, hamster, porcine, bovine, feline, or canine. Mammalian cells can also be cells of primates, including but not limited to, monkeys, chimpanzees, gorillas, and humans. Mammalians cells can be mouse cells, as mice routinely function as a model for other mammals, most particularly for humans (see, e.g., Hanna, J. et al., Science 318:1920-23, 2007; Holtzman, D. M. et al., J Clin Invest. 103(6):R15-R21, 1999; Warren, R. S. et al., J Clin Invest. 95: 1789-1797, 1995; each publication is incorporated by reference in its entirety for all purposes). Host cells include, for example, fibroblasts, epithelial cells (e.g., renal, mammary, prostate, lung), keratinocytes, hepatocytes, adipocytes, endothelial cells, and hematopoietic cells (e.g., macrophages, other monocytes, antigen presenting cells, B-cells, neutrophils, mast cells, dendritic cells, or other phagocytosing cell types). The host cells can be adult cells (e.g., terminally differentiated, dividing or nondividing) or embryonic cells (e.g., blastocyst cells, etc.) or stem cells. The host cell can be a cell line derived from an animal or other source.

The mammalian cell can be a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells. Such circulating cells can be primary cells or derived from primary cells. The circulating cells may be autologous, syngeneic or allogeneic. Mammalian cells can be derived from any of these circulating eukaryotic cells. Circulating cells or cells derived from the circulating cells can be used. The mammalian cell can be a macrophage or a precursor or progenitor cell to a macrophage. The monocyte or macrophage cell can be a raw 264.7 cell, a K562 cell or a THP-1 cell. The mammalian cell can be a T-cell or T-cell precursor or progenitor cell. The mammalian cell can be a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. The mammalian cell can be a natural killer cell, or a precursor or progenitor cell to the natural killer cell. The mammalian cell can be a B-cell, or a plasma cell, or a B-cell precursor or progenitor cell. The mammalian cell can be a neutrophil or a neutrophil precursor or progenitor cell. The mammalian cell can be a megakaryocyte or a precursor or progenitor cell to the megakaryocyte. The mammalian cell can be an antigen presenting cell such as a monocyte, macrophage, dendritic cell, epithelial cell, etc. The APC can be engineered to lack MHC molecules on its surface. Such an APC will only display MHC molecules from the MHC:antigen fusion polypeptide of the antigen library.

Any immune cell that can be used as the host cells herein including, for example, T-cells, B-cells, Natural Killer cells, dendritic cells, macrophages, monocytes, and/or neutrophils. Host cells can be receptor specific immune cells or cell lines genetically modified to express target receptors. Host cells include human primary immune cells, mouse primary immune cells, rat primary immune cells, and immortalized mammalian cell lines. Examples of immortalized mammalian cell lines that can be used include Jurkat, K562, Tall-104, Raji, HEK293, HEK293T, 3T6, A559, A9, AtT-20, 3T3, BHK-21, BHL-100, BT, Caco-2, Chang, CHO-K1, COS-1, COS-3, COS-7, Daudi, H9, HeLa, Hep-2, HL-60, HT-1080, HT-29, HUVEC, I-10, IM-9, JEG-2, MDA-MB-231, L2, KB, KG-1, MCF7, WI-38, WISH, XC, Y1, Jeko, NK-92, NK-92 MI, J76, CCRF-CEM, DND-41, HPB-ALL, MOL-4, RPMI-8402, GRANTA, MINO, REC-1, U-2940, BJAB, VAL, THP-1, MUTZ-3, U-937, ME-1, MOLM13, U-937, and SEM.

The host cell can be obtained from a subject. The subject may be any living organism. Examples of subjects include humans, dogs, cats, mice, rats, and transgenic species thereof. Macrophages, T-cells, antigen presenting cells etc. can be obtained from a number of sources, including peripheral blood mononuclear cells, bone marrow, lymph node tissue, cord blood, thymus tissue, tissue from a site of infection, ascites, pleural effusion, spleen tissue, and tumors. Any number of macrophage cell lines, antigen presenting cell lines, or T cell lines are available in the art, and can be used. Macrophages, antigen presenting cells, or T cells can be obtained from a unit of blood collected from a subject using any number of techniques known to the skilled artisan, such as Ficoll separation. Host cells from the circulating blood of an individual can be obtained by apheresis. The apheresis product typically contains lymphocytes, including T cells, monocytes, granulocytes, B cells, other nucleated white blood cells, red blood cells, and platelets. Cells collected by apheresis may be washed to remove the plasma fraction and to place the cells in an appropriate buffer or media for subsequent processing steps. Cells can be washed with phosphate buffered saline (PBS). In an alternative aspect, the wash solution lacks calcium and may lack magnesium or may lack many if not all divalent cations. Initial activation steps in the absence of calcium can lead to magnified activation.

In an aspect, the genome of the host cell is engineered with a first nucleic acid that has a unique site for insertion of an insert nucleic acid by a targeting system such as CRISPR. The host cell can optionally be engineered with an enzyme of a targeting system including, for example, Cas9, Cas12a (aka Cpf1), an appropriate zinc-finger nuclease (ZFN), or a transcription-activator-like nuclease (TALEN). The first nucleic acid can be engineered to be close to or adjacent to the nucleic acids encoding the receptor or binding protein in the host cell. This allows directed insertion of nucleic acids to this site near or next to the nucleic acid encoding the receptor. When the antigen/ligand interacts with the receptor/binding protein of the host cell this can introduce a nucleic acid into the host cell. When this nucleic acid is accompanied by an appropriate targeting nucleic acid (e.g., a guide RNA) the nucleic acid representing the antigen/ligand can be integrated near or next to the nucleic acid encoding the receptor. For example, the pegRNA described herein can insert into this site. Appropriate primers will amplify and/or sequence both the nucleic acid (or bar code) for the receptor and the nucleic acid (or bar code) for the antigen/ligand.

Nucleic Acids

Nucleic acids can encode, at least in part, the individual peptides, polypeptides, proteins, and barcodes described herein. Nucleic acids may be natural, synthetic or a combination thereof. Nucleic acids may be RNA, mRNA, DNA or cDNA.

Nucleic acids also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. Exemplary selection schemes can utilize a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

An example of a promoter that is capable of expressing a transgene encoding an TCR or an antigen described herein in a mammalian host cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the expression vectors herein are not limited to the use of constitutive promoters.

Inducible promoters are also contemplated for use in expression vectors. Examples of inducible promoters include, but are not limited to a metallothionine promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822, 754, 8,748,125, 8,536,354, all of which are incorporated by reference in their entirety for all purposes.

Expression vectors typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

It may be desirable to modify the polypeptides described herein. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, Gene 8:81-97, 1979; Roberts et al., Nature 328:731-734, 1987, which is incorporated by reference in its entirety for all purposes). The recombinant nucleic acids encoding the polypeptides described herein can be modified to provide preferred codons which enhance translation of the nucleic acid in a selected organism.

The polynucleotides of the invention also include polynucleotides including nucleotide sequences that are substantially equivalent to the polynucleotides described herein. Polynucleotides can have at least about 80%, more typically at least about 90%, and even more typically at least about 95%, sequence identity to a polynucleotide encoding a polypeptide of interest. Polynucleotides include the complement of polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants (i.e., wherein one or more amino acids are designed to differ from the wild-type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., Angew Chem Intl Ed. 28:716-34, 1989 (which is incorporated by reference in its entirety for all purposes), may also be used to prepare such nucleic acids.

Amino acid "substitutions" for creating variants can be the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Nucleic acids can be linked to another nucleic acid so as to be expressed under control of a suitable promoter. Nucleic acids can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid, a gene that can be a marker for confirming expression of the nucleic acid (e.g. a drug resistance gene, a gene encoding a reporter enzyme, or a gene encoding a fluorescent protein) may be incorporated.

When the nucleic acid is introduced into a cell ex vivo, the nucleic acid may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid is also useful. Particularly, a composition in a form suitable for administration to a living body which contains the nucleic acid carried by a suitable vector is suitable for in vivo gene therapy.

Introduction of Polynucleotides to Host Cells

Nucleic acids can be introduced to the eukaryotic cell by transfection (e.g., Gorman, et al. Proc. Natl. Acad. Sci. 79.22 (1982): 6777-6781, which is incorporated by reference in its entirety for all purposes), transduction (e.g., Cepko and Pear (2001) Current Protocols in Molecular Biology unit 9.9; DOI: 10.1002/0471142727.mb0909s36, which is incorporated by reference in its entirety for all purposes), calcium phosphate transformation (e.g., Kingston, Chen and Okayama (2001) Current Protocols in Molecular Biology Appendix 1C; DOI: 10.1002/0471142301.nsa01cs01, which is incorporated by reference in its entirety for all purposes), calcium chloride and polyethylene glycol (PEG) to introduce recombinant DNA into microalgal cells (see Kim et al., (2002) Mar. Biotechnol. 4:63-73, which reports the use of this method to transform Chlorella elhpsoidea protoplasts, and which is incorporated by reference in its entirety for all purposes), cell-penetrating peptides (e.g., Copolovici, Langel, Eriste, and Langel (2014) ACS Nano 2014 8 (3), 1972-1994; DOI: 10.1021/nn4057269, which is incorporated by reference in its entirety for all purposes), electroporation (e.g Potter (2001) Current Protocols in Molecular Biology unit 10.15; DOI: 10.1002/0471142735.im1015s03 and Kim et al (2014) Genome 1012-19. doi:10.1101/gr.171322.113, Kim et al. 2014 describe the Amaza Nucleofector, an optimized electroporation system, both of these references are incorporated by reference in their entirety for all purposes), microinjection(e.g., McNeil (2001) Current Protocols in Cell Biology unit 20.1; DOI: 10.1002/0471143030.cb2001s18, which is incorporated by reference in its entirety for all purposes), liposome or cell fusion (e.g., Hawley-Nelson and Ciccarone (2001) Current Protocols in Neuroscience Appendix 1F; DOI: 10.1002/0471142301.nsa01fs10, which is incorporated by reference in its entirety for all purposes), mechanical manipulation (e.g. Sharon et al. (2013) PNAS 2013 110(6); DOI: 10.1073/pnas.1218705110, which is incorporated by reference in its entirety for all purposes), biolistic methods (see, for example, Sanford, Trends in Biotech. (1988) 6: 299 302, U.S. Pat. No. 4,945,050, which is incorporated by reference in its entirety for all purposes), Lithium Acetate/PEG transformation (Gietz and Woods (2006) Methods Mol. Biol. 313, 107-120) and its modifications, which is incorporated by reference in its entirety for all purposes, or other well-known techniques for delivery of nucleic acids to host cells. Once introduced, the nucleic acids of the invention can be expressed episomally, or can be integrated into the genome of the host cell using well known techniques such as recombination (e.g., Lisby and Rothstein (2015) Cold Spring Harb Perspect Biol. March 2; 7(3). pii: a016535. doi: 10.1101/cshperspect.a016535, which is incorporated by reference in its entirety for all purposes), non-homologous integration (e.g., Deyle and Russell (2009) Curr Opin Mol Ther. 2009 August; 11(4):442-7, which is incorporated by reference in its entirety for all purposes) or transposition (as described above for mobile genetic elements). The efficiency of homologous and non-homologous recombination can be facilitated by genome editing technologies that introduce targeted single or double-stranded breaks (DSB). Examples of DSB-generating technologies are CRISPR/Cas9, TALEN, Zinc-Finger Nuclease, or equivalent systems (e.g., Cong et al. Science 339.6121 (2013): 819-823, Li et al. *Nucl. Acids Res* (2011): gkr188, Gaj et al. Trends in Biotechnology 31.7 (2013): 397-405, all of which are incorporated by reference in their entirety for all purposes), transposons such as Sleeping Beauty (e.g., Singh et al (2014) Immunol Rev. 2014 January; 257(1):181-90. doi: 10.1111/imr.12137, which is incorporated by reference in its entirety for all purposes), targeted recombination using, for example, FLP recombinase (e.g., O'Gorman, Fox and Wahl Science (1991) 15:251(4999):1351-1355, which is incorporated by reference in its entirety for all purposes), CRE-LOX (e.g., Sauer and Henderson *PNAS* (1988): 85; 5166-5170), or equivalent systems, or other techniques known in the art for integrating the nucleic acids of the invention into the eukaryotic cell genome.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

Novel Receptors

T-cell receptors and the corresponding antigen/ligands are found by mixing a TCR repertoire as described herein with an antigen library as described herein, separating individual cells with a chimeric TCR which cells have phagocytosed a cell with a certain antigen-MHC fusion protein. Alternatively, T-cell receptors and the corresponding antigen/ligands are found by mixing a TCR repertoire as described herein with an antigen library as described herein, separating individual cells with trogocytosis markers and antigen/TCR barcodes. For example, the cells with the antigen library can be labeled with an optical probe, and optionally the cells with the TCR repertoire can be labeled with a different optical probe. FACs sorting can then be used to isolate cells from the TCR repertoire that obtain antigen barcodes from the antigen library. The separated cells are then sequenced to identify the TCR and the antigen pair. Sequencing can be performed to identify the TCR and antigen. For example, sequencing can identify the barcodes associated with each TCR and each antigen, or the TCR and the antigen fusion can be sequenced in whole or in part. The high throughput of these systems and these methods will allow the identification of TCRs and the antigens to which the TCR binds. The TCRs identified will include many novel TCRs not known to interact with antigens of interest.

The methods and compositions described herein can be used to find novel TCRs useful in treating cancers, infectious diseases, autoimmune diseases, etc. Target antigens associated with these diseases are known and can be used to find novel TCRs that interact with the antigens. The TCRs identified by these methods can be used to produce immunotherapies for treating these diseases. For example, many tumor associated antigens (TAA) are known. The methods and compositions described herein can produce antigen libraries from the TAA which can be used to find TCRs that bind to the TAA. These TCRs can be used to make chimeric TCRS and/or chimeric antigen receptors that target cytotoxic T-cells and Natural Killer cells to the cancer cells. Similarly, many antigens are known for various infectious diseases. The methods and compositions described here can identify TCRs that can be used to treat these infectious diseases. For example, chimeric TCRs combining the TCR ligand binding portion with an Fc signaling portion (and optionally co-activators) can be used to make macrophages or other phagocytic cells that will phagocytose the microbial agent that causes the infectious disease. Alternatively, chimeric TCRs or chimeric antigen receptors trigger T-cell activation, trogocytosis and antigen/TCR barcode exchange. The TCRs can also be used to make chimeric antigen receptors that can activate T-helper cells to lyse tumor cells, activate the tumor microenvironment, or assist B-cells in producing neutralizing antibodies.

Exemplary tumor associated antigens are the KRAS variant alleles associate with certain cancers. More than 90% of pancreatic cancers, and 30% of lung, colon and bile duct cancers have one of these KRAS variant alleles. KRAS variant alleles include, for example, G12D, G12V, G12R, G12H, G12S, G12L, Q61H, Q61K, Q61R, A11T, G13P, G13D, and the double mutant G12D and Q61H. An antigen library is made with some or all of these mutant KRAS variant alleles focusing on the peptides that include the mutation for presentation by the antigen library. Many different T-cell receptor repertoires can be combined with the KRAS antigen library to find TCRs that bind to the different KRAS variant alleles. T-cell receptor repertoires used can be sourced from genomic libraries of TCRs, or TCRs from cancer patients who have survived the cancer of interest (e.g., pancreatic cancer, or lung cancer, or colon cancer, or bile duct cancer). TCR repertoires can be made from patients who have received an immunotherapy and survived (or had partial responses) indicating that the patient's immune system was able to combat the cancer.

The anti-KRAS variant TCRs can be assessed for their ability to discriminate between the different KRAS variant alleles and the wild-type KRAS. Affinity of the anti-KRAS variant TCRs for the KRAS variants and the wild-type can also be assessed. The anti-KRAS variant T-cell receptors can be stratified into groups based on these characteristics, and the anti-KRAS variant T-cell receptors can be used to make chimeric antigen receptors for immunotherapy.

Other tumor associated antigens include, for example, mesothelin, disialoganglioside (GD2), Her-2, MUC1, GPC3, EGFRVIII, CEA, CD19, EGFR, PSMA, GPC2, folate receptor β, IgG Fc receptor, PSCA, PD-L1, EPCAM, Lewis Y Antigen, L1CAM, FOLR, CD30, CD20, EPHA2, PD-1, C-MET, ROR1, CLDN18.2, NKG2D, CD133, TSHR, CD70, ERBB, AXL, Death Receptor 5, VEGFR-2, CD123, CD80, CD86, TSHR, ROR2, CD147, kappa IGG, IL-13, MUC16, IL-13R, NY-ESO-1, IL13RA2, DLL3, FAP, LMP1, TSHR, BCMA, NECTIN-4, MG7, AFP (alpha-fetoprotein), GP100, B7-H3, Nectin-4, MAGE-A1, MAGE-A4, MART-1, HBV, MAGE-A3, TAA, GP100, Thyroglobulin, EBV, HPV E6, PRAME, HERV-E, WT1, GRAS G12V, p53, TRAIL, MAGE-A10, HPV-E7, KRAS G12D, MAGE-A6, CD19, BCMA, CD22, CD123, CD20, CD30, CD33, CD138, CD38, CD7, SLAMF7, IGGFC, MUC1, Lewis Y Antigen, CD133, ROR1, FLT3, NKG2D, Kappa light chain, CD34, CLL-1, TSLP, CD10, PD-L1, CD44V6, EBV, CD5, GPC3, CD56, integrin B7, CD70, MUCL, CKIT, CLDN18.2, TRBC1, TAC1, CD56, CD4, CD2, CD18, CD27, CD37, CD72, CD79A, CD79B, CD83, CD117, CD172, ERBB3, ERBB4, DR5, HER2, CS1, IL-1RAP, ITGB7, SLC2A14, SLC4A1, SLC6A11, SLC7A3, SLC13A5, SLC19A1, SLC22A12, SLC34A1, slc45A3, SLC46A2, Fra, IL-13Ra2, ULBP3, ULBP1, CLD18, NANOG, CEACAM8, TSPAN16, GLRB, DYRK4, SV2C, SIGLEC8, RBMXL3, HIST1HIT, CCR8, CCNB3, ALPPL2, ZP2, OTUB2, LILRA4, GRM2, PGG1, NBIF3, GYPA, ALPP, SPATA19, FCRLI, FCRLA, CACNG3, UPK3B, 12UMO4, MUC12, HEPACAM, BPI, ATP6V0A4, HMMR, UPK1A, ADGRV1, HERC5, C3AR1, FASLG, NGB, CELSR3, CD3G, CEACAM3, TNFRSFBC, MS4AB, S1PR5, EDNRB, SCN3A, ABCC8, ABCB1, ANO1, KCND2, HTR4, CACNB4, HTR4, CNR2, 26LRB, EXOC1, ENTPP1, ICAM3, ABCGB, SCN4B, SPN, CD68, ITGAL, ITGAM, SCTR, CYYR1, CLCN2, SLARA3, and JAG3.

Other tumor associated antigens include, for example, complement factor H (e.g., lung cancer, breast cancer, other solid tumors), delta opioid receptor (e.g., small cell lung cancer), c-Met (e.g., NSCLC), gpNMB (e.g., melanoma, breast cancer, other solid tumors), TRAP-2 (e.g., epithelial tumors and other solid tumors), CEACAM5 (e.g., colorectal cancer), CD56 (e.g., SCLC), CD25 (e.g., hematological cancers), guanyl cyclase C (e.g., pancreatic cancer), CAG (e.g., solid tumors), LIV-1 (e.g., breast cancer), PTK7 (e.g., lung cancer, colorectal cancer, breast cancer, and ovarian cancer), LAMP-1 (e.g., colorectal cancer, melanoma, laryngeal cancer), P-cadherin 3 (e.g., epithelial tumors), HER-3 (e.g., breast cancer), CD133 (e.g., hepatocellular carcinoma, pancreatic cancer, colorectal cancer, cholangiocarcinoma), GPRC5D (e.g., multiple myeloma), BCMA (e.g., multiple myeloma), CD138 (e.g., multiple myeloma), Ig kappa light chain (e.g., leukemia, lymphoma, NHL, and multiple myeloma), CD30 (e.g., NHL, HD), IL13Ra2 (e.g., glioblastoma), and ligands for NKG2D (e.g., using the NKG2D receptor as the binding domain for, e.g., AML, MDS, and MM).

Alternatively, the retroviruses described above can be used with a host cell displaying a receptor or other binding molecule on it surface. The retroviruses (displaying antigens/ligands) and a population of host cells are combined (e.g., physically combined or contacted). The population of host cells can be sorted based on the presence or absence of the reporter (encoded in the nucleic acid carried by the retrovirus). A subset of the population of host cells containing the reporter (e.g., express the reporter) can be sorted from the remaining subset of the population of host cells that do not contain the reporter. Sorting of the population of cells can be performed using flow cytometry (e.g., fluorescence-activated cell sorting), magnetic enrichment, or antibiotic selection. This FACs or other sorting separates host cells infected by the retrovirus from host cells which are not infected (do not have the retrovirus nucleic acid).

A lentivirus or retrovirus can carry several genetic components to be expressed after infection of the host cells: 1) genetic sequences of the antigen/ligand, 2) prime editing guide RNA (pegRNA) including a barcode in the template region, 3) reporter gene (e.g., a reporter such as GFP) to indicate presence of viral transduction, and 4) other helper protein (e.g., MEW). These genetic components will be expressed in host cells with the receptor or binding protein (e.g. T-cells). The retrovirus (e.g., lentivirus) can display potential antigen/ligands and helper protein necessary for binding to the receptor or binding protein on the host cell. The reporter gene (e.g. GFP) is expressed by the host cells infected by the retrovirus (e.g., lentivirus) allowing infected host cells to be screened and sorted (for example with FACs) from host cells that are not infected. The retrovirus (e.g., lentivirus) vector delivers pegRNA that serves two functions: 1) targeting the CRISPR editing complex to specific insertion sites based on sequence homology with the unique site integrated near or next to the nucleic acid encoding the receptor or binding protein, and 2) inserting retrovirus (e.g., lentivirus) nucleic acid (e.g., a barcode sequence) into the specific insert site via homology-based repair.

The construct to be packaged in the retrovirus (e.g., lentivirus) can have constant regions and two variable regions. One variable region encodes a barcode to be inserted with the pegRNA scaffold in the target site in the host cell. The second variable region encodes variable regions of antigen/ligand to interact with receptors/binding proteins, e.g., S-ETD-LGD-IRES-R, wherein S encodes a signal sequence, ETD encodes an extracellular targeting domain; LGD encodes the antigen/ligand, IRES encodes an internal ribosome entry site, and R encodes a reporter (e.g., a fluorescent protein or antibiotic resistance). The IRES and M are optional, and the nucleic acid can encode S-ETD-LGD. Nucleotide sequences can be inserted into these two variable regions simultaneously or sequentially via Type-I restriction digestion based assembly, Golden Gate Assembly, Gateway Assembly or Gibson Assembly. When using Type I restriction digestion based assembly, two different digestion enzymes will be used for each variable region. When using Golden Gate Assembly, four Type IIs restriction digestion sites can be introduced to allow inserting barcode and antigen nucleotide sequences simultaneously.

The fusogen for the viral constructs is engineered to allow cell-to-cell membrane fusion only upon antigen/ligand-receptor (or binding protein) interaction. One example of such fusogens is a mutated vesicular stomatitis virus G protein (VSV-G). VSV-G is a viral envelope protein that has been extensively used to pseudotype lentiviruses. Example mutations are K47Q and R354A to prevent its direct recognition and interaction with LDLR on host cells (Nikolic et al., 2018 CITE, which is incorporated by reference in its entirety for all purposes). Now the VSV-G can mediate cell entry based on a user-defined ligand-receptor interaction.

Lentivirus and/or retrovirus can use host cell membranes as their own viral membrane during budding, thus any protein present on the production cell membrane can be displayed by the viral particle. Production cells can present full antigen/ligand protein on their cell membranes as long as the lentivirus and/or retrovirus construct contains antigen/ligand protein sequences and the antigen/ligand proteins are membrane bound. Many ligands are naturally membrane proteins (e.g. PD-L1 and MHC-antigen complex). Antigens/Ligands which are not naturally membrane bound can be anchored to the cell membrane by fusing it to a transmembrane domain DNA sequence, such as a viral coat protein. Exemplary transmembrane domains include wildtype or modified transmembrane domains from CD2, CD3d, CD3g, CD3z, CD4, CD8A, CD8B, CD22, CD27, CD28, CD40, CD79a, CD79b, CD80, CD84, CD86, CD137, CD244, CRACC, CRTAM, CLTA-4, MHC-I, MHC-II, platelet-derived growth factor receptor, FCGR1A, FCGR2A, FCG2B, FCGR3A, FCRL1, FCRL2, FCRL3, FCRL4, FCRL5,

37

FCRL6, KIR2DL1, KIR2DL2, KIR2DL3, KIR2DL4, KIR2DL5A, KIR2DL5B, KIR3DL1, KIR3DL2, KIR3DL3, LAG3, GITR, OX40, PD-1, PD-L1, PD-L2, TLR, SLAMF, LILRB1, LILRB2, NKG2A, NKG2C, NKG2D, TIGIT, IgG, IgM, IgA, IgE, IgD, or immunoglobulin.

MHC-antigen complexes can be displayed on the retrovirus (e.g., lentivirus) using a single chain trimer (Mottez et al., Cells expressing a major histocompatibility complex class I molecule with a single covalently bound peptide are highly immunogenic, J. Exp. Med. 181:493-502 (1995), which is incorporated by reference in its entirety for all purposes). A single chain trimer can have a signal peptide, antigen peptide, a linker, MHC beta chain, a second linker and MHC alpha chain in tandem. For example, DNA that encodes human growth hormone signal peptide to beta2 microglobulin (MHC beta chain) can be synthesized and inserted into lentiviral constructs together with the MHC alpha chain. Co-transfecting the packaging cell line (293T) with a single chain trimer DNA (part of our lentivirus and retrovirus plasmid) will produce membrane bound MHC-antigen complexes. As lentivirus and retrovirus use packaging cell membranes as their viral membrane, MHC-antigen complexes can be presented on the viral membrane.

The Reporter (e.g., reporter such as GFP) can be introduced into host cells in two ways to indicate viral entrance: 1) lentivirus or retrovirus carries pre-translated reporter gene product (protein), 2) lentivirus or retrovirus delivers and integrates reporter gene into receptor cell genomes. An exemplary way to carry reporter gene product with viruses is fusing GFP with a virus structure protein (e.g. viral envelop protein or M protein). Lentivirus and retrovirus naturally deliver the construct with the reporter into host cell genomes.

After producing the lentivirus or retrovirus with packaging cells, the virus suspension can be mixed with the receptor host library. Lentivirus or retrovirus will infect the receptor host cell when there is a correct antigen/ligand-receptor/binding protein pair between them. Lentivirus or retrovirus deliver viral RNA and relevant proteins (reverse transcriptase and/or reporter protein) into receptor cells. Viral RNA or viral DNA integrated via reverse transcriptase can produce reporter gene product (e.g., GFP) and pegRNA (barcode sequence).

The pegRNA can introduce the barcode into a specific site in the receptor host cell genome (e.g. a region near or next to the receptor gene) by interacting with Cas9 or Cas12a or other gene editing enzymes. CRISPR editing enzymes can be produced by host cells, lentivirus viral DNA, or introduced via electroporation. The barcode can then be sequenced with the receptor (and/or its barcode) to identify the antigen/ligand and receptor/binding protein pair.

PegRNA can have three components: 1) a scaffold region (also known as constant region), 2) a sequence targeting region, and 3) a barcode region. The sequence target region is specific for an insertion site in the host cell. 1 e0 to 1 e5 sequence target regions can be used to target multiple regions of the receptor host cells though each individual pegRNA can only target one region. Barcode regions determine specific sequences to be inserted into the insertion site. 1 e0-1 e10 different barcodes can be used. Sequence targeting region and barcode region are nearby each other on viral plasmid, thus they can use the same cloning site or separate cloning sites.

Infected cells can be isolated based on the reporter gene product (GFP), for example using flow cytometry FACS or magnetic bead pull down. Magnetic beads can be conjugated to a protein or antibody that can bind to surface reporter protein (e.g. MYC-tag or FLAG-tag). Cells bound to magnetic beads are enriched for infected cells.

These enriched host cells can be bulk, high throughput sequenced to identify the receptor/binding protein and the antigen/ligand. This sequencing identifies the pegRNA barcode to identify the antigen/ligand binding to the receptor. As pegRNA is inserted near or nest to the receptor gene, either conventional sequencing (100-600 nt long) or long read sequencing (600-30,000 nt) can be performed to capture the relationship between antigen/ligand barcode and the receptor/binding protein. As barcode-ligand relationship can be established previously by construct bulk sequencing, binding pairs can be computationally inferred.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1: Making TCR Mimics Like Chimeric TCRs or Chimeric Antigen Receptors (CAR)

Single chain T-cell receptors are made according to Zhang et al., Cancer Gene Therapy 11:487-496 (2004), which is incorporated by reference in its entirety for all purposes. Appropriate cytoplasmic regions are fused with the single chain TCRs to make the chimeric T-cell receptors. Cytoplasmic regions include one or more of an Fc cytoplasmic domain, CD3ζ, CD28, B7.1, CD137, CD19 intracellular activation domain, CD64 intracellular activation domain, CD32 intracellular activation domain, CD16 intracellular activation domain, CD23 intracellular activation domain, or Lck activation domain.

The single chain or natural double chain TCRs or natural double chain TCRs are made from the T-cell receptors Flu-TCR1, Flu-TCR2, DMF-5, 1G4, CSS-944-8, CSS-930-1a, CSS-930-1b, PMEL-1, PMEL-2 and PMEL-3. Certain sequences of the alpha and beta TCR chains for each of these TCRs are in the Tables 3 and 4 below:

TABLE 3

| TCR Alpha Chains | | | |
|---|---|---|---|
| Name | TCRA V | TCRA J | TCRA CDR3 |
| Flu-TCR 1 | TRAV27 | TRAJ42 | CAGAGSQGNLIF (SEQ ID NO: 6) |
| Flu-TCR 2 | TRAV27 | TRAJ37 | CAGAIGSSNTGKLIF (SEQ ID NO: 7) |
| DMF-5 | TRAV12-2*01 | TRAJ23*01 | CAVNFGGGKLIF (SEQ ID NO: 8) |
| 1G4 | TRAV21 | TRAJ6 | CAVRPTSGGSYIPTF (SEQ ID NO: 9) |
| CSS-944-8 | TRAV3 | TRAJ26 | CAGYYGQNFVF (SEQ ID NO: 10) |
| CSS-930-1 | TRAV12-1 | TRAJ34 | CVVRTDKLIF (SEQ ID NO: 11) |

TABLE 3-continued

| TCR Alpha Chains | | | |
|---|---|---|---|
| Name | TCRA V | TCRA J | TCRA CDR3 |
| CSS-930-1 | TRAV1-1 | TRAJ20 | CAVRDNDYKLSF (SEQ ID NO: 12) |
| PMEL-1 | TRAV30 | TRAJ48 | CGIGNEKLTF (SEQ ID NO: 13) |
| PMEL-2 | TRAV12-2 | TRAJ24 | CAVSTDSWGKLQF (SEQ ID NO: 14) |
| PMEL-3 | TRAV35 | TRAJ30 | CAPGGDDKIIF (SEQ ID NO: 15) |

TABLE 4

| TCR Beta Chains | | | |
|---|---|---|---|
| Name | TCRB V | TCRB J | TCRB CDR3 |
| Flu-TCR 1 | TRBV19 | TRBJ2-7 | CASSSRSSYEQYF (SEQ ID NO: 16) |
| Flu-TCR 2 | TRBV19 | TRBJ2-7 | CASSIRSSYEQYF (SEQ ID NO: 17) |
| DMF-5 | TRBV6-4*01 | TRBJ1-1*01 | CASSLSFGTEAFF (SEQ ID NO: 18) |
| 1G4 | TRBV6-5 | TRBJ2-2 | CASSYVGNTGELFF (SEQ ID NO: 19) |
| CSS-944-8 | TRBV28 | TRBJ1-1 | CASSFQGYTEAFF (SEQ ID NO: 20) |
| CSS-930-1 | TRBV5-1 | TRBJ1-3 | CASSLDSQSSGNTIYF (SEQ ID NO: 21) |
| CSS-930-1 | TRBV5-1 | TRBJ2-7 | CASSLEGQASSYEQYF (SEQ ID NO: 22) |
| PMEL-1 | TRBV7-6 | TRBJ2-3 | CGIGNEKLTF (SEQ ID NO: 23) |
| PMEL-2 | TRBV7-6 | TRBJ2-7 | CAVSTDSWGKLQF (SEQ ID NO: 24) |
| PMEL-3 | TRBV7-6 | TRBJ2-1 | CAPGGDDKIIF (SEQ ID NO: 25) |

Some of the TCRs and their antigens are described in Spindler et al, Nature Biotechnol. 38:609-619 (2020).

Multiple chimeric antigen receptors are made for each single chain TCR. The TCR CDR3 region and its flanking regions (~150 nt) serve as a barcode for TCR identification.

TCR repertoires can also include TCR sequences identified in human donor tissues (including blood), modified natural human TCR sequences, or TCR sequences generated by computer algorithm. To enhance success rate of screening, one of the following approaches can be used to select TCR sequences: selecting TCRs from donors with HLA allele of interest, selecting donors with conditions of interest (e.g. CMV status or cancer status, or using HLA predicting algorithms based on the TCR sequence.

Example 2: A Repertoire of TCRs in THP-1 Cells

A repertoire of chimeric TCRs made in Example 1 are engineered into THP-1 cells. The constructs encoding the chimeric TCRs are introduced so that individual THP-1 cells carry one construct and express one chimeric TCR. A population of THP-1 cells with the repertoire of chimeric TCRs can be used in subsequent steps.

Example 3: A Repertoire of TCRs in Jurkat Cells

A repertoire of chimeric TCRs made in Example 1 are engineered into Jurkat cells. The constructs encoding the chimeric TCRs are introduced so that individual Jurkat cells carry one construct and express one chimeric TCR. A population of Jurkat cells with the repertoire of chimeric TCRs can be used in subsequent steps.

Example 3: An Antigen Library in K562 Cells

An antigen library is made from appropriate influenza HLA, human MART-1, epitope NY-ESO-1 (SLLMWITQC (SEQ ID NO:26)), LMP2(CLG), pMHC dextramer for A2/PMEL(KTW), gp100, and for the T-cell receptors Flu-TCR1, Flu-TCR2, DMF-5, 1G4, CSS-944-8, CSS-930-1a, CSS-930-1b, PMEL-1, PMEL-2 and PMEL-3. HLA gene and antigen sequences can be fused into a single peptide or encoded as separate peptides. HLA alpha and beta chains can be fused or encoded as separate peptides. Antigen sequences are 8-25 amino acids long, as HLA can only bind and present a fragment of a full protein. A computer algorithm selects peptides to use as presentable antigens, other epitopes are previously reported in IEDB (iedb.org), e.g., Vita et al., The Immune Epitope Database (IEDB): 2018 update, which are incorporated by reference in their entirety for all purposes. Antigen barcodes of antigen presentation cells can be introduced simultaneously or sequentially with the antigen coding DNA or RNA. Antigen barcodes made of either DNA or RNA can be attached to cell membrane via DNA or RNA binding proteins can be engineered zinc finger nuclease, transcription factor binding protein, replication protein A, CRSIPR Cas9, Cpf1, Cas13, phage RNA binding proteins, bacterial single strand binding protein, or engineered restriction digestion enzymes.

For a full data-generating experiment, a repertoire of antigen sequences (>100) is introduced into K562 cells. Antigen sequences can be peptide sequences identified in in vitro binding experiments, mass spectrometry experiments, sliding windows of protein sequences (8-25 per window), or fragments of known proteins predicted to be presentable with a computer algorithm. This computer algorithm is trained on either in vitro binding data, mass spectrometry data, or gene expression data to identify sequences likely to be presented by MHC/HLA complexes.

Example 4: Screening the Chimeric T-Cell Receptor Repertoire Against the Antigen Library THP-1 cells with the TCR repertoire and K562 cells with the antigen library are each also labeled with different fluorescent proteins or live dye restricted to their nuclei. THP-1 cells with the chimeric TCR repertoire are mixed with K562 cells with the antigen library, and THP-1 cells can phagocytose K562 cells displaying the MHC:antigen fusion recognized by the chimeric TCR. After incubation, all cells are analyzed with flow cytometry and cell sorting to isolate cells with both fluorescent signals (showing that a THP-1 cell and K562 cell are together). Cells with the two different fluorescent signals are THP-1 cells that have engulfed K562 cells. This cell population is sequenced with either bulk or single cell DNA sequencing. Primers are used to amplify the antigen encoding region (antigen barcode) and CDR3 regions (TCR barcodes). From bulk sequencing, the binding pairs of antigens and TCR sequences are identified.

From single cell sequencing, paired antigens and TCR sequences involved in activation events can be identified. Frequency of antigen or TCR reads can be used to identify the most likely interacting pairs.

Example 5: Screening the T-Cell Receptor Repertoire Against the Antigen Library

Jurkat cells with the TCR repertoire and K562 cells with the antigen library are each also labeled with different membrane bound fluorescent proteins or live dye. In addition, the TCR repertoire and the antigen library are engineered with an appropriate binding motif for a nucleic acid binding protein. The Jurkat cells and the K562 cells are engineered with a fusion protein of a nucleic acid binding protein and a synthetic transmembrane domain so that the nucleic acid binding domain is present on the cytoplasmic side of the membrane. Jurkat cells with the chimeric TCR repertoire are mixed with K562 cells with the antigen library, and Jurkat cells can trogocytose membrane pieces from the K562 cells displaying the MHC:antigen fusion recognized by the chimeric TCR (the K562 cells can also trogocytose pieces of the Kurkat cell membranes). After incubation, all cells are analyzed with flow cytometry and cell sorting to isolate cells with both fluorescent signals (showing that Jurkat cells have trogocytosed K562 cell membrane). Cells with the two different fluorescent signals are Jurkat cells that have been activated by K562 cells. Portions of the nucleic acids encoding the antigen and the TCR are sequenced with either bulk or single cell DNA sequencing. Primers are used to amplify the antigen encoding region (and/or an antigen barcode) and CDR3 regions (and/or a TCR barcode). From bulk sequencing, the binding pairs of antigens and TCR sequences are identified.

From single cell sequencing, paired antigens and TCR sequences involved in activation events can be identified. Frequency of antigen or TCR reads can be used to identify the most likely interacting pairs.

Example 6: Screening of T-Cell Receptor Repertoire Against Retrovirus Antigen Library Jurkat cells with the TCR repertoire as described above are used in this example. These Jurkat cells are engineered to express Cas12a. Lentiviral constructs are engineered with pegRNA and antigen-MHC complexes fused with a GFP. The PegRNA targets the lentiviral construct to a sequence near the TCR gene in the Jurkat cell genome. The PegRNA includes a barcode sequence that can be a 15 nucleotide long random sequence (theoretical diversity of 1 e9). The PegRNA sequence is expressed by an U6 promoter and terminated by polyT sequences. The lentiviral construct expresses a library of antigen-MHC complexes introduced as single chain trimers fused with a GFP. The lentiviral particles display the antigen MHC complex library on different viral particles. Expression of the MHC single chain trimer is controlled by a mammalian gene promoter (e.g. EF1a promoter). Antigen diversity is 1 e5 and can be tuned based on the application. The MHC allele can be any human MHC allele or any human MHC allele with mutations. Both barcode and ligand sequence region contain PaqCI cloning sites (thus four PaqCI cutting sites with different cutting site sequences). Barcode and ligand sequences can be introduced into the lentiviral construct library via Golden Gate Assembly. After plasmid amplification, 1% of construct material has the pegRNA-antigen region sequenced to established barcode-antigen pairings.

The lentiviral construct is packaged by HEK293T packaging cells engineered with packaging helper plasmids (e.g. Gag-pol plasmid and VSV-G plasmid). The VSV-G plasmid contains mutations in the coding region for VSV-G which disable VSV-G direct interaction with LDLR on T-cells but still allows viral entrance when antigen-TCR interaction bring the virus into proximity to a cell. A virus suspension is collected 48 h and 72 h post transfection of the packaging cell line. Membrane-bound GFP signal is checked to confirmed MHC single chain trimer fused with GFP is normally displayed on the cell surface and virus surface.

The library of lentiviral particles with the MHC-antigen library are used to transfect a population of Jurkat cells with the TCR repertoire. The PegRNA of the lentiviral construct targets the construct for insertion into the Jurkat genome adjacent to the human TRBC1 (TCR beta constant region 1), TRBC2 (TCR beta constant region 2) and/or TRAC (TCR alpha constant region). Transduced Jurkat cells are identified and sorted by detecting GFP signal on flow cytometry FACS device. Live cell dye can be used to remove dead cells to reduce false positive signal for GFP. Sorted Jurkat cells with GFP expression are pooled and lysed to extract DNA. The DNA is sequenced using amplification primers for the TCR and the lentivirus barcode. Purified PCR product is sequenced in a bulk-sequencing format via long read sequencing (e.g. PacBio HiFi long-read sequencing). Pair-relationships between TCR sequences and antigen barcodes can be established by ranking the frequency of common TCR-antigen pairs compared to background distributions. Background distributions can be established via computational modeling or sequencing negative control samples.

Optionally target antigens identified by sequencing can validated as follows. Antigens can be introduced to an WIC allele matched antigen-presenting cell line (APCs, e.g. primary B-cells, T2 cells, or K562 cells) via DNA plasmid, mRNA, peptide, or whole protein. T-cell lines with the TCR of interest can be mixed the antigen-presenting APCs and T-cell activation markers can be measured via imaging, ELISA or flow cytometry. T-cell activation markers include IL-2, TNF-alpha, IFN-gamma, NFAT mediated transcription activities, AP-1 mediated transcription activities, NF-kB mediated transcription activities, CD69, CD107a, CD137 (4-1BB), HLA-DR, CD38, trogocytosis, PD-1, CD25, CD71 and morphology changes. Correct target antigens for a TCR activate the T-cells as measured by one or more of the markers described above after the co-incubation of T-cells and APCs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

Those skilled in the art will recognize or be able to ascertain using no more than routine experimentation, many equivalents to the specific embodiments of the invention described herein. Such equivalents are intended to be encompassed by the following claims.

SEQUENCE LISTING

Sequence total quantity: 26

SEQ ID NO: 1          moltype = DNA   length = 11
FEATURE               Location/Qualifiers
source                1..11
                      mol_type = other DNA
                      organism = synthetic construct
SEQUENCE: 1
attgcacaat a                                                          11

SEQ ID NO: 2          moltype = RNA   length = 19
FEATURE               Location/Qualifiers
source                1..19
                      mol_type = other RNA
                      organism = synthetic construct
SEQUENCE: 2
gggccctgaa gaagggccc                                                  19

SEQ ID NO: 3          moltype = RNA   length = 17
FEATURE               Location/Qualifiers
source                1..17
                      mol_type = other RNA
                      organism = synthetic construct
SEQUENCE: 3
tgcgctgaca aagcgcg                                                    17

SEQ ID NO: 4          moltype = RNA   length = 19
FEATURE               Location/Qualifiers
source                1..19
                      mol_type = other RNA
                      organism = synthetic construct
SEQUENCE: 4
acatgaggat tacccatgt                                                  19

SEQ ID NO: 5          moltype = RNA   length = 19
FEATURE               Location/Qualifiers
source                1..19
                      mol_type = other RNA
                      organism = synthetic construct
SEQUENCE: 5
agttcagcat tagcgaact                                                  19

SEQ ID NO: 6          moltype = AA   length = 12
FEATURE               Location/Qualifiers
source                1..12
                      mol_type = protein
                      organism = Homo sapiens
SEQUENCE: 6
CAGAGSQGNL IF                                                         12

SEQ ID NO: 7          moltype = AA   length = 15
FEATURE               Location/Qualifiers
source                1..15
                      mol_type = protein
                      organism = Homo sapiens
SEQUENCE: 7
CAGAIGSSNT GKLIF                                                      15

SEQ ID NO: 8          moltype = AA   length = 12
FEATURE               Location/Qualifiers
source                1..12
                      mol_type = protein
                      organism = Homo sapiens
SEQUENCE: 8
CAVNFGGGKL IF                                                         12

SEQ ID NO: 9          moltype = AA   length = 15
FEATURE               Location/Qualifiers
source                1..15
                      mol_type = protein
                      organism = Homo sapiens
SEQUENCE: 9
CAVRPTSGGS YIPTF                                                      15

SEQ ID NO: 10         moltype = AA   length = 11
FEATURE               Location/Qualifiers
source                1..11
                      mol_type = protein
                      organism = Homo sapiens

```
SEQUENCE: 10
CAGYYGQNFV F                                                             11

SEQ ID NO: 11        moltype = AA   length = 10
FEATURE              Location/Qualifiers
source               1..10
                     mol_type = protein
                     organism = Homo sapiens
SEQUENCE: 11
CVVRTDKLIF                                                               10

SEQ ID NO: 12        moltype = AA   length = 12
FEATURE              Location/Qualifiers
source               1..12
                     mol_type = protein
                     organism = Homo sapiens
SEQUENCE: 12
CAVRDNDYKL SF                                                            12

SEQ ID NO: 13        moltype = AA   length = 10
FEATURE              Location/Qualifiers
source               1..10
                     mol_type = protein
                     organism = Homo sapiens
SEQUENCE: 13
CGIGNEKLTF                                                               10

SEQ ID NO: 14        moltype = AA   length = 13
FEATURE              Location/Qualifiers
source               1..13
                     mol_type = protein
                     organism = Homo sapiens
SEQUENCE: 14
CAVSTDSWGK LQF                                                           13

SEQ ID NO: 15        moltype = AA   length = 11
FEATURE              Location/Qualifiers
source               1..11
                     mol_type = protein
                     organism = Homo sapiens
SEQUENCE: 15
CAPGGDDKII F                                                             11

SEQ ID NO: 16        moltype = AA   length = 13
FEATURE              Location/Qualifiers
source               1..13
                     mol_type = protein
                     organism = Homo sapiens
SEQUENCE: 16
CASSSRSSYE QYF                                                           13

SEQ ID NO: 17        moltype = AA   length = 13
FEATURE              Location/Qualifiers
source               1..13
                     mol_type = protein
                     organism = Homo sapiens
SEQUENCE: 17
CASSIRSSYE QYF                                                           13

SEQ ID NO: 18        moltype = AA   length = 13
FEATURE              Location/Qualifiers
source               1..13
                     mol_type = protein
                     organism = Homo sapiens
SEQUENCE: 18
CASSLSFGTE AFF                                                           13

SEQ ID NO: 19        moltype = AA   length = 14
FEATURE              Location/Qualifiers
source               1..14
                     mol_type = protein
                     organism = Homo sapiens
SEQUENCE: 19
CASSYVGNTG ELFF                                                          14

SEQ ID NO: 20        moltype = AA   length = 13
FEATURE              Location/Qualifiers
source               1..13
                     mol_type = protein
```

-continued

```
                         organism = Homo sapiens
SEQUENCE: 20
CASSFQGYTE AFF                                                      13

SEQ ID NO: 21           moltype = AA   length = 16
FEATURE                 Location/Qualifiers
source                  1..16
                        mol_type = protein
                        organism = Homo sapiens
SEQUENCE: 21
CASSLDSQSS GNTIYF                                                   16

SEQ ID NO: 22           moltype = AA   length = 16
FEATURE                 Location/Qualifiers
source                  1..16
                        mol_type = protein
                        organism = Homo sapiens
SEQUENCE: 22
CASSLEGQAS SYEQYF                                                   16

SEQ ID NO: 23           moltype = AA   length = 10
FEATURE                 Location/Qualifiers
source                  1..10
                        mol_type = protein
                        organism = Homo sapiens
SEQUENCE: 23
CGIGNEKLTF                                                          10

SEQ ID NO: 24           moltype = AA   length = 13
FEATURE                 Location/Qualifiers
source                  1..13
                        mol_type = protein
                        organism = Homo sapiens
SEQUENCE: 24
CAVSTDSWGK LQF                                                      13

SEQ ID NO: 25           moltype = AA   length = 11
FEATURE                 Location/Qualifiers
source                  1..11
                        mol_type = protein
                        organism = Homo sapiens
SEQUENCE: 25
CAPGGDDKII F                                                        11

SEQ ID NO: 26           moltype = AA   length = 9
FEATURE                 Location/Qualifiers
source                  1..9
                        mol_type = protein
                        organism = Homo sapiens
SEQUENCE: 26
SLLMWITQC                                                           9
```

We claims:

1. A method for obtaining a T-cell receptor or a T-cell receptor mimic, comprising the steps of: mixing a plurality of macrophage cells comprising a first plurality of nucleic acids encoding a repertoire of chimeric T-cell receptors or T-cell receptor mimics with a plurality of antigen presenting cells comprising an optical reporter and a second plurality of nucleic acids encoding an antigen library, wherein the antigens in the antigen library are fusions of a MHC molecule with a peptide from an antigen; expressing the plurality of nucleic acids encoding the repertoire of chimeric T-cell receptors in the plurality of macrophage cells;

expressing the plurality of nucleic acids encoding the antigen library in the plurality of antigen presenting cells; isolating a macrophage cell that has phagocytosed an antigen presenting cell;

and sequencing the first plurality of nucleic acids and the second plurality of nucleic acids.

2. The method of claim 1, wherein the first plurality of nucleic acids further comprises a plurality of different nucleic acid bar codes, wherein each T-cell receptor or T-cell receptor mimic is associated with a different bar code.

3. The method of claim 1, wherein the second plurality of nucleic acids further comprises a plurality of different nucleic acid bar codes, wherein each antigen is associated with a different bar code.

4. The method of claim 2, wherein the sequencing of the first plurality of nucleic acids sequences the bar code.

5. The method of claim 3, wherein the sequencing of the second plurality of nucleic acids sequences the bar code.

6. The method of claim 2, wherein the second plurality of nucleic acids further comprises a plurality of different nucleic acid bar codes, wherein each antigen is associated with a different bar code.

7. The method of claim 6, wherein the sequencing of the first plurality of nucleic acids sequences the bar code, and wherein the sequencing of the second plurality of nucleic acids sequences the bar code.

8. The method of claim 1, wherein the chimeric T-cell receptors comprise a single chain T-cell receptor fused with an Fc cytoplasmic domain.

9. The method of claim 1, wherein the repertoire of T-cell receptors are derived from a genomic DNA of a plurality of T-cells from a subject or from a plurality of cDNAs from a plurality of T-cells obtained from a subject.

10. The method of claim 8, wherein the repertoire of T-cell receptors or T-cell receptor mimics are derived from a genomic DNA of a plurality of embryonic T-cells.

11. The method of claim 1, wherein the repertoire of T-cell receptors or T-cell receptor mimics is obtained from a subject that is naïve to the antigen library.

12. The method of claim 1, wherein the repertoire of T-cell receptors or T-cell receptor mimics is obtained from a subject that has mounted an immune response to an antigen from the antigen library.

13. The method of claim 1, wherein the antigen library is a plurality of cancer associated antigens.

14. The method of claim 13, wherein the cancer associated antigen is from a pancreatic cancer, a lung cancer, a colon cancer, or a bile duct cancer.

15. The method of claim 14, wherein the cancer associated antigen is a KRAS variant allele.

16. The method of claim 15, wherein the KRAS variant allele is a G12D, a G12V, a G12R, a G12H, a G12S, a G12L, a Q61H, a Q61K, a Q61R, an A11T, a G13P, a G13D, or a double mutant G12D and Q61H.

17. The method of claim 13, wherein the cancer associated antigen is a tumor neoantigen.

18. The method of claim 1, wherein the antigen library is a plurality of infectious disease associated antigens.

19. The method of claim 18, wherein the infectious disease is caused by a bacterial pathogen.

20. The method of claim 18, wherein the infectious disease is caused by a viral pathogen.

*   *   *   *   *